US011974913B2

(12) United States Patent
Armstrong et al.

(10) Patent No.: US 11,974,913 B2
(45) Date of Patent: May 7, 2024

(54) PROSTHETIC VALVED CONDUIT

(71) Applicant: EDWARDS LIFESCIENCES CORPORATION, Irvine, CA (US)

(72) Inventors: Joseph R. Armstrong, Flagstaff, AZ (US); Nathan L. Bennett, Flagstaff, AZ (US); Kyle W. Colavito, Flagstaff, AZ (US); Edwin W. Field, Flagstaff, AZ (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/115,219

(22) Filed: Feb. 28, 2023

(65) Prior Publication Data

US 2023/0363895 A1    Nov. 16, 2023

Related U.S. Application Data

(63) Continuation of application No. 16/714,055, filed on Dec. 13, 2019, now Pat. No. 11,617,644, which is a continuation of application No. 14/881,124, filed on Oct. 12, 2015, now Pat. No. 10,507,101.

(60) Provisional application No. 62/063,353, filed on Oct. 13, 2014.

(51) Int. Cl.
*A61F 2/24* (2006.01)

(52) U.S. Cl.
CPC .......... *A61F 2/2412* (2013.01); *A61F 2/2409* (2013.01); *A61F 2/2415* (2013.01); *A61F 2/2418* (2013.01); *A61F 2220/005* (2013.01); *A61F 2220/0058* (2013.01); *A61F 2220/0075* (2013.01); *A61F 2230/0069* (2013.01); *A61F 2230/008* (2013.01); *A61F 2250/0098* (2013.01)

(58) Field of Classification Search
CPC ........ A61F 2/06; A61F 2/2412; A61F 2/2418; A61F 2240/001; A61F 2/2409; A61F 2/2475; A61F 2/07; A61F 2/82
See application file for complete search history.

(56) References Cited

U.S. PATENT DOCUMENTS

| | | |
|---|---|---|
| 3,997,923 A | 12/1976 | Possis |
| 4,218,782 A | 8/1980 | Rygg |
| 4,692,164 A | 9/1987 | Dzemeshkevich et al. |
| 4,747,848 A | 5/1988 | Maini |
| 5,123,919 A | 6/1992 | Sauter et al. |
| 5,139,515 A | 8/1992 | Robicsek |
| 5,197,979 A | 3/1993 | Quintero et al. |

(Continued)

FOREIGN PATENT DOCUMENTS

| | | |
|---|---|---|
| EP | 0169259 A1 | 1/1986 |
| EP | 2478871 A2 | 7/2012 |

(Continued)

OTHER PUBLICATIONS

US 8,075,613, 10/1994, Danielson et al. (withdrawn)

*Primary Examiner* — Seema Mathew
(74) *Attorney, Agent, or Firm* — Alan T. Hale; Chang & Hale LLP

(57) ABSTRACT

Prosthetic valved conduits are provided that include a leaflet construct coupled between two portions of a conduit. Each leaflet has a free edge and a leaflet attachment edge. The leaflet attachment edge is disposed between a first conduit distal end and a second conduit proximal end that are coaxial therebetween defining a junction.

10 Claims, 22 Drawing Sheets

(56) References Cited

U.S. PATENT DOCUMENTS

| | | | |
|---|---|---|---|
| 5,376,112 A | 12/1994 | Duran | |
| 5,489,297 A * | 2/1996 | Duran | A61F 2/2418 623/2.13 |
| 5,545,215 A * | 8/1996 | Duran | A61F 2/2415 623/1.26 |
| 5,814,096 A | 9/1998 | Lam et al. | |
| 5,862,806 A | 1/1999 | Cheung | |
| 5,891,195 A | 4/1999 | Klostermeyer et al. | |
| 6,001,126 A | 12/1999 | Nguyen-Thien-Nhon | |
| 6,090,140 A | 7/2000 | Gabbay | |
| 6,264,691 B1 | 7/2001 | Gabbay | |
| 6,299,638 B1 | 10/2001 | Sauter | |
| 6,352,554 B2 * | 3/2002 | De Paulis | A61F 2/06 623/1.29 |
| 6,364,905 B1 * | 4/2002 | Simpson | A61F 2/2415 623/2.15 |
| 6,390,447 B1 | 5/2002 | Mosher | |
| 6,482,228 B1 | 11/2002 | Norred | |
| 6,783,556 B1 | 8/2004 | Gabbay | |
| 6,875,230 B1 | 4/2005 | Morita et al. | |
| 6,976,952 B1 | 12/2005 | Maini et al. | |
| 7,018,404 B2 | 3/2006 | Holmberg et al. | |
| 7,137,184 B2 * | 11/2006 | Schreck | A61F 2/2412 29/469 |
| 7,186,265 B2 * | 3/2007 | Sharkawy | A61F 2/2418 623/2.38 |
| 7,261,732 B2 | 8/2007 | Justino | |
| 7,422,603 B2 | 9/2008 | Lane | |
| 7,488,346 B2 | 2/2009 | Navia | |
| 7,575,592 B2 | 8/2009 | Woo | |
| 7,618,447 B2 | 11/2009 | Case et al. | |
| 7,625,403 B2 | 12/2009 | Krivoruchko | |
| 7,641,686 B2 | 1/2010 | Lashinski et al. | |
| 7,641,687 B2 | 1/2010 | Chinn et al. | |
| 7,686,844 B2 | 3/2010 | Case et al. | |
| 7,717,952 B2 | 5/2010 | Case et al. | |
| 7,806,920 B2 | 10/2010 | Duran | |
| 7,854,759 B2 * | 12/2010 | Shirley | A61B 17/12172 623/2.14 |
| 7,972,376 B1 | 7/2011 | Dove et al. | |
| 8,303,647 B2 * | 11/2012 | Case | A61F 2/2475 623/2.14 |
| 9,138,314 B2 * | 9/2015 | Rolando | A61F 2/2427 |
| 9,301,835 B2 * | 4/2016 | Campbell | A61L 27/3687 |
| 9,844,436 B2 * | 12/2017 | De Paulis | A61F 2/2427 |
| 9,987,132 B1 | 6/2018 | Hariton | A61F 2/2415 |
| 10,507,101 B2 * | 12/2019 | Armstrong | A61F 2/2409 |
| 10,940,167 B2 * | 3/2021 | Kassab | A61F 2/2415 |
| 10,980,633 B2 * | 4/2021 | Dienno | A61F 2/2412 |
| 11,039,919 B2 * | 6/2021 | Colavito | A61L 27/56 |
| 11,179,237 B2 * | 11/2021 | Rolando | A61F 2/2412 |
| 2001/0049553 A1 * | 12/2001 | De Paulis | A61F 2/2403 623/1.24 |
| 2003/0139805 A1 * | 7/2003 | Holmberg | A61F 2/2403 623/1.26 |
| 2003/0187500 A1 * | 10/2003 | Jansen | B29C 41/08 264/250 |
| 2004/0193242 A1 | 9/2004 | Lentz et al. | |
| 2004/0254640 A1 * | 12/2004 | Sutherland | A61F 2/2412 435/399 |
| 2005/0143810 A1 | 6/2005 | Dauner et al. | |
| 2005/0222675 A1 | 10/2005 | Sauter | |
| 2005/0234546 A1 * | 10/2005 | Nugent | A61F 2/2433 623/2.11 |
| 2005/0267559 A1 | 12/2005 | De Oliveira | |
| 2006/0085060 A1 * | 4/2006 | Campbell | A61F 2/2412 623/2.4 |
| 2006/0167386 A1 | 7/2006 | Drake et al. | |
| 2006/0271081 A1 | 11/2006 | Realyvasquez | |
| 2008/0082161 A1 * | 4/2008 | Woo | A61F 2/2412 623/1.26 |
| 2008/0091261 A1 * | 4/2008 | Long | A61F 2/2475 623/1.24 |
| 2008/0147171 A1 | 6/2008 | Ashton et al. | |
| 2009/0093873 A1 | 4/2009 | Navia | |
| 2009/0264993 A1 | 10/2009 | Greenan | |
| 2010/0185277 A1 * | 7/2010 | Braido | A61F 2/2433 623/2.37 |
| 2010/0274351 A1 * | 10/2010 | Rolando | A61F 2/2412 623/1.26 |
| 2011/0112620 A1 * | 5/2011 | Du | D03D 3/06 623/1.1 |
| 2011/0214398 A1 | 9/2011 | Liburd et al. | |
| 2012/0010697 A1 | 1/2012 | Shin et al. | |
| 2012/0185038 A1 * | 7/2012 | Fish | A61F 2/2415 493/405 |
| 2013/0046379 A1 * | 2/2013 | Paolitto | A61F 2/2412 623/2.19 |
| 2013/0172991 A1 * | 7/2013 | Rolando | A61F 2/243 623/2.11 |
| 2013/0325111 A1 * | 12/2013 | Campbell | A61L 27/3625 623/2.11 |
| 2014/0012371 A1 * | 1/2014 | Li | A61F 2/2418 264/273 |
| 2014/0121764 A1 * | 5/2014 | De Paulis | A61F 2/2496 623/2.11 |
| 2014/0128960 A1 * | 5/2014 | Greenslet | B29C 39/003 623/2.12 |
| 2014/0155995 A1 * | 6/2014 | Sun | A61F 2/2418 623/2.18 |
| 2014/0172078 A1 * | 6/2014 | Bruchman | A61F 2/2409 156/185 |
| 2015/0119980 A1 * | 4/2015 | Beith | A61F 2/2418 623/2.18 |
| 2016/0074151 A1 * | 3/2016 | Pfeiffer | A61F 2/0805 623/13.17 |
| 2016/0100939 A1 * | 4/2016 | Armstrong | A61F 2/2412 623/2.12 |

FOREIGN PATENT DOCUMENTS

| | | |
|---|---|---|
| WO | 03007795 A2 | 1/2003 |
| WO | 2006/013234 A1 | 2/2006 |

* cited by examiner

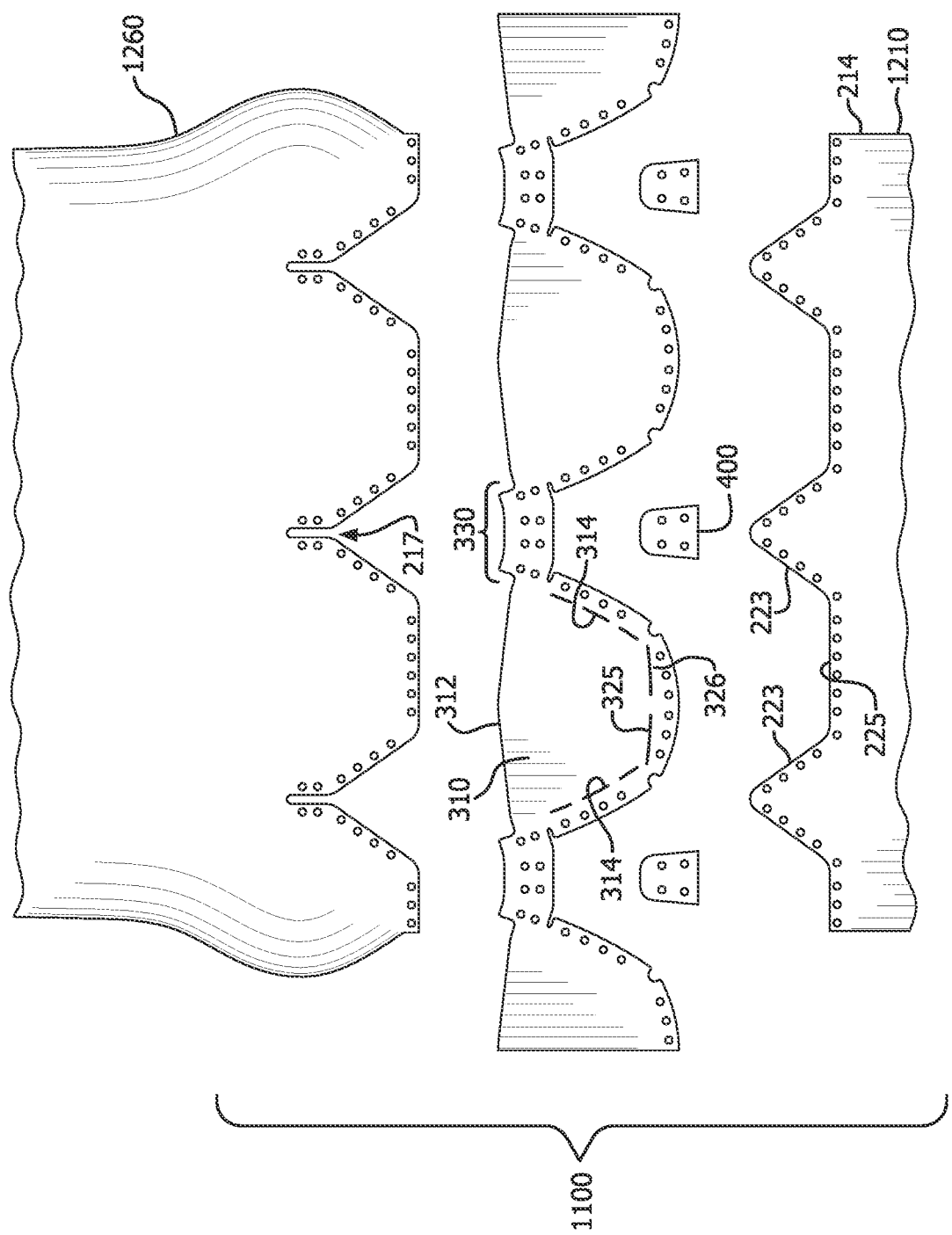

PROSTHETIC VALVED CONDUIT

CROSS-REFERENCE TO RELATED APPLICATION

This application is a continuation of U.S. patent application Ser. No. 16/714,055, filed Dec. 13, 2019, which is a continuation of U.S. patent application Ser. No. 14/881,124, filed Oct. 12, 2015, now U.S. Pat. No. 10,507,101, issued Dec. 17, 2019, which claims the benefit of U.S. Provisional Application 62/063,353, filed Oct. 13, 2014, which are incorporated herein by reference in their entireties for all purposes.

FIELD

The present disclosure relates generally to prosthetic valves and more specifically to conduits having a valve structure therein.

BACKGROUND

A number of fabrication techniques have been used to couple leaflets to the inside of a conduit, including sewing individual leaflets to the inner surface of the conduit. In many cases, the resulting leaflet is supported on the inside surface of the conduit and defines a flap having a mounting edge where the leaflet is coupled to the inside surface of the conduit and a free edge that allows the flap to move. The flap moves under the influence of fluid pressure. In operation, the leaflets open when the upstream fluid pressure exceeds the downstream fluid pressure allowing flow through the conduit and closes when the downstream fluid pressure exceeds the upstream fluid pressure and blocks the flow through the conduit.

The process for mounting the leaflet to the inside surface of the conduit is tedious, time consuming and requires great skill. The conduit is everted to expose the inside surface of the conduit. The leaflet is precisely cut to the correct size and shape. The attachment edge of the leaflet is sewn by hand onto the everted conduit. Additional leaflets, commonly three total, are sewn circumferentially around the everted conduit. Once attached to the inside surface of the conduit, the conduit is reverted with the expectation that the three leaflets are properly placed. The three leaflets must cooperate with each other such that they may coapt at their free edges to create a seal and prevent flow during the closed phase of the cardiac cycle.

Valved conduits made in this way present significant challenges. The leaflets must be precisely cut to size and shape prior to attachment. Placement of the leaflets on the inside surface of the conduit while in an everted state and relative to the other leaflets must be held to high tolerances, usually placed by hand with without alignment tools or jigs. The punctures of the attachment edge with a needle for receiving suture not only have to be precisely placed by hand, but the number of punctures must be limited to reduce structural weakening along the attachment edge. Further, all of the punctures and resulting suture passing therethrough is exposed to the blood flow and are located precisely at the line of flexure of the leaflet at the leaflet base, which can lead to reduced durability.

Leaflet durability under the repetitive loads of the leaflets opening and closing is dependent, in part, on the load distribution between the leaflet and the conduit wall. Further, substantial load is encountered on the leaflet when in the closed position. Mechanical failure of the leaflet can arise, for example, at the mounting edge, where the flexible leaflet is attached by the suture, particularly at the commissure region. The repetitive loads of the leaflet opening and closing leads to material failure by fatigue, creep or other mechanism, depending in part on the leaflet material. Mechanical failure at the mounting edge is especially prevalent with synthetic leaflets.

Therefore, there remains a significant need for a valved conduit, encompassing a conduit and a valve structure, with long durability and easier manufacture.

SUMMARY

Described embodiments are directed to apparatus, system, and methods for valved conduits.

Embodiments of a valved conduit comprise a first conduit having a first conduit distal end, a second conduit having a second conduit proximal end, and a valve structure including at least one leaflet. Each leaflet has a free edge and a leaflet attachment edge. The leaflet attachment edge is disposed between the first conduit distal end and the second conduit proximal end that are coaxial therebetween defining a junction. The leaflet attachment edge is coupled between the first conduit distal end and the second conduit proximal end.

Embodiments of a method of making a valved conduit, comprise obtaining a conduit. Cutting the conduit into a first conduit and a second conduit along a cut line defining a first conduit distal end and a second conduit proximal end. Defining a plurality of commissure slots in the second conduit proximal end. Obtaining a tube comprising one or more layers of expanded PTFE composite. Cutting a leaflet construct including a plurality of leaflets each being separated by a bridge region from the tube, the leaflets defining a leaflet attachment edge. Folding each of the bridge regions into a bridge loop and defining a coaptation neck between each bridge loop and two adjacent leaflets, the bridge loops extending radially away from a tube axis. Disposing a bridge loop into each of the commissure slots, and suturing the first conduit distal end and the second conduit proximal end with the leaflet attachment edge therebetween defining a junction.

Embodiments of a method of making a valved conduit, comprise obtaining a conduit, either as a tube, a flat sheet, or a flat sheet formed into a tube. Cutting the conduit into a first conduit and a second conduit along a cut line defining a first conduit distal end and a second conduit proximal end. Defining a plurality of commissure slots in the second conduit proximal end. Obtaining a sheet comprising one or more layers of expanded PTFE composite. Cutting a leaflet construct including one or a plurality of leaflets each being separated by a bridge region or a pair of commissure tabs from the sheet, the leaflets defining a leaflet attachment edge. Folding each of the bridge regions or commissure tabs defining a coaptation neck between each bridge region and two adjacent leaflets or commissure tabs, the bridge regions or commissure tabs extending radially away from a tube axis. Disposing a bridge region or commissure tabs into each of the commissure slots, and suturing the first conduit distal end and the second conduit proximal end with the leaflet attachment edge therebetween defining a junction.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

FIG. 8 is a representation of the embodiment of FIG. 7 laid flat, in the case of a tube, longitudinally cut and laid open to a flat orientation;

DETAILED DESCRIPTION

Figure 1A:
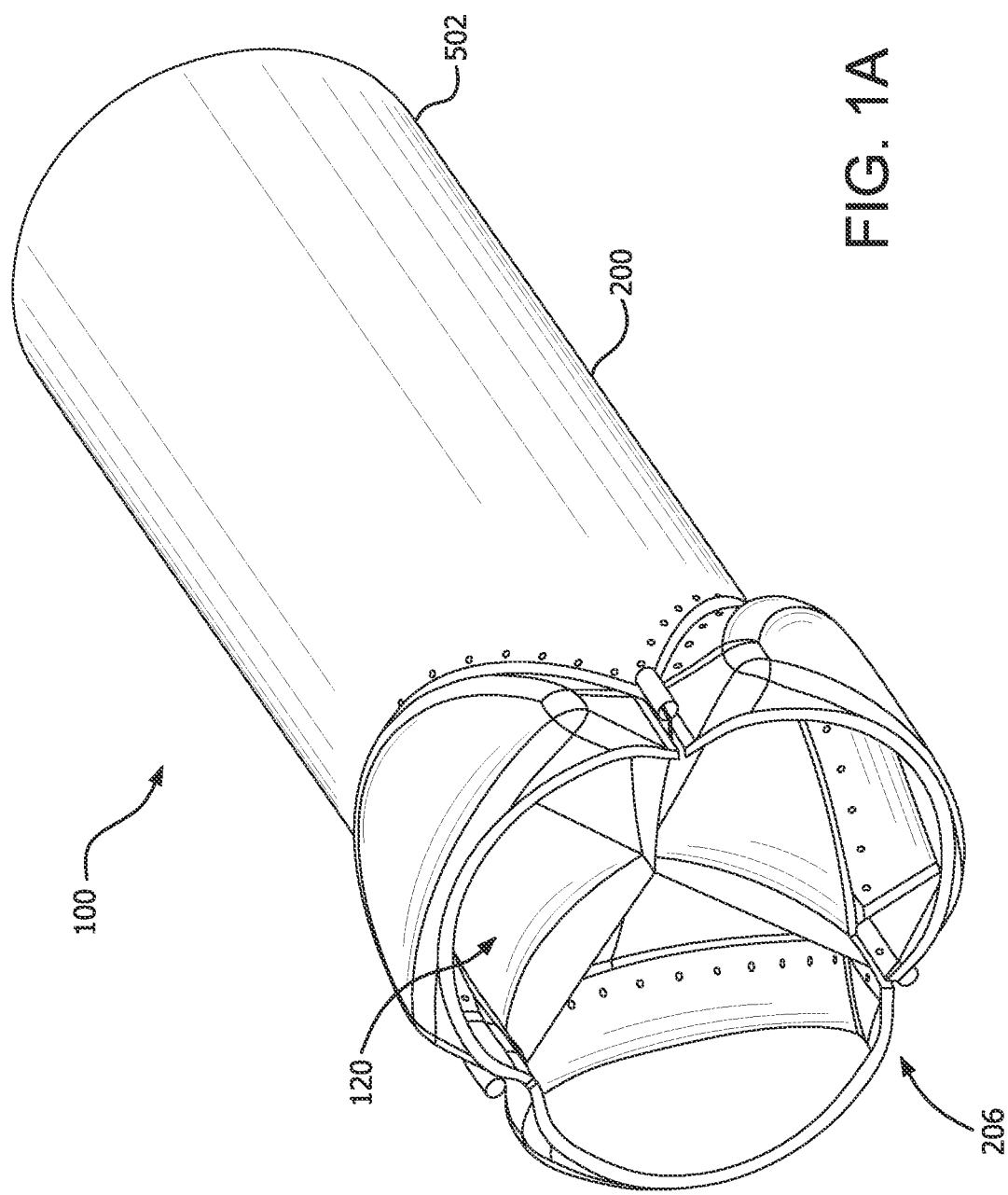
FIG. 1A is a perspective, partial cut-away view of an embodiment of a valved conduit including a valve structure as disposed in the conduit.

Persons skilled in the art will readily appreciate that various aspects of the present disclosure can be realized by any number of methods and apparatus configured to perform the intended functions. Stated differently, other methods and apparatus can be incorporated herein to perform the intended functions. It should also be noted that the accompanying figures referred to herein are not necessarily drawn to scale, but may be exaggerated to illustrate various aspects of the present disclosure, and in that regard, the figures should not be construed as limiting.

Although the embodiments herein may be described in connection with various principles and beliefs, the described embodiments should not be bound by theory. For example, embodiments are described herein in connection with prosthetic valved conduits. However, embodiments within the scope of this disclosure can be applied toward any valved conduit, valve structure, or mechanism of similar structure and/or function. Furthermore, embodiments within the scope of this disclosure can be applied in non-cardiac applications.

The term "leaflet", as used herein in the context of a valved conduit, is a flexible component of a one-way valve structure wherein the leaflet is operable to move between an open and closed position under the influence of a fluid pressure differential. In an open position, the leaflet allows blood to flow through the valve structure. In a closed position, the leaflet substantially blocks retrograde flow through the valve structure. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one surface of the leaflets when closed. As the pressure on an inflow surface of the valve structure rises above the pressure on the outflow surface of the valve structure, the leaflets open and blood flows therethrough. As blood flows through the valve structure into a neighboring chamber or blood vessel, the pressure on the inflow surface of the valve structure equalizes with the pressure on the outflow surface of the valve structure. As the pressure on the outflow surface of the valve structure raises above the blood pressure on the inflow surface of the valve structure, the leaflet returns to the closed position generally preventing retrograde flow of blood through the valve structure.

The term "valved conduit", as used herein, is defined as a conduit with a valve structure that is within the conduit for use in coronary or vascular procedures.

The term "valve structure", as used herein, is defined as one or more separate leaflets or a leaflet construct having a plurality of leaflets that are coupled together that function as a one-way valve.

The term "leaflet construct", as used herein, is defined as a valved structure comprising a plurality of leaflets that are coupled together with a commissure region between each leaflet.

The term "sinus", as used herein, is defined as a region of a conduit that has a larger inner diameter than a surrounding region. A sinus may be utilized to create an open volume behind and downstream from an open leaflet such that the open leaflet does not lie against the inner surface of the conduit. The sinus may direct the blood to flow between the conduit inner surface and the open leaflet during forward flow to prevent blood pooling behind the leaflet, and may assist in moving the leaflet from the open position to a closed position during reversed flow conditions. The sinus may also be described as having a shape of a bulge or concavity especially when viewed from the conduit inner surface.

The term "membrane", as used herein, refers to a sheet comprising a single material, such as, but not limited to, expanded fluoropolymer.

The term "composite material", as used herein, refers to a combination of a membrane, such as, but not limited to, expanded fluoropolymer, and an elastomer, such as, but not limited to, a fluoroelastomer. The elastomer can be contained within a porous structure of the membrane, coated on one or both surfaces of the membrane, or a combination of coated on and contained within the porous structure of the membrane.

The term "laminate", as used herein, refers to multiple layers of membrane, composite material, or other materials, such as elastomer, and combinations thereof.

The term "film", as used herein, generically refers to one or more of the membrane, composite material, or laminate.

The term "biocompatible material", as used herein, generically refers to any material with biocompatible characteristics including synthetic, such as, but not limited to, a biocompatible polymer, or a biological material, such as, but not limited to, bovine pericardium.

The term "coupled", as used herein, means joined, connected, attached, adhered, affixed, or bonded, whether directly or indirectly, and whether permanently or temporarily.

Embodiments herein include various apparatus, systems, and methods for a conduit having a valve structure operable as a prosthetic valve that can be used, such as, but not limited to, replace a pulmonary valve and a portion of the corresponding pulmonary artery. The leaflet is operable as a one-way valve wherein the conduit defines a conduit lumen into which the leaflets open to permit flow and close so as to occlude the conduit lumen and prevent flow in response to differential fluid pressure.

FIG. 1A is a perspective, partial cut-away view of an embodiment of a valved conduit 100 including a valve structure 120 as disposed in the conduit 200. The partial cut-away view of the valved conduit 200 shows a portion of the valved conduit 100 that is slightly downstream of the valve structure 120, shown in a closed configuration. An upstream end 502 of the valved conduit 100 may be positioned in a patient's vasculature or cardiac structure to receive blood flowing to the valve structure 120.

Figure 1B:
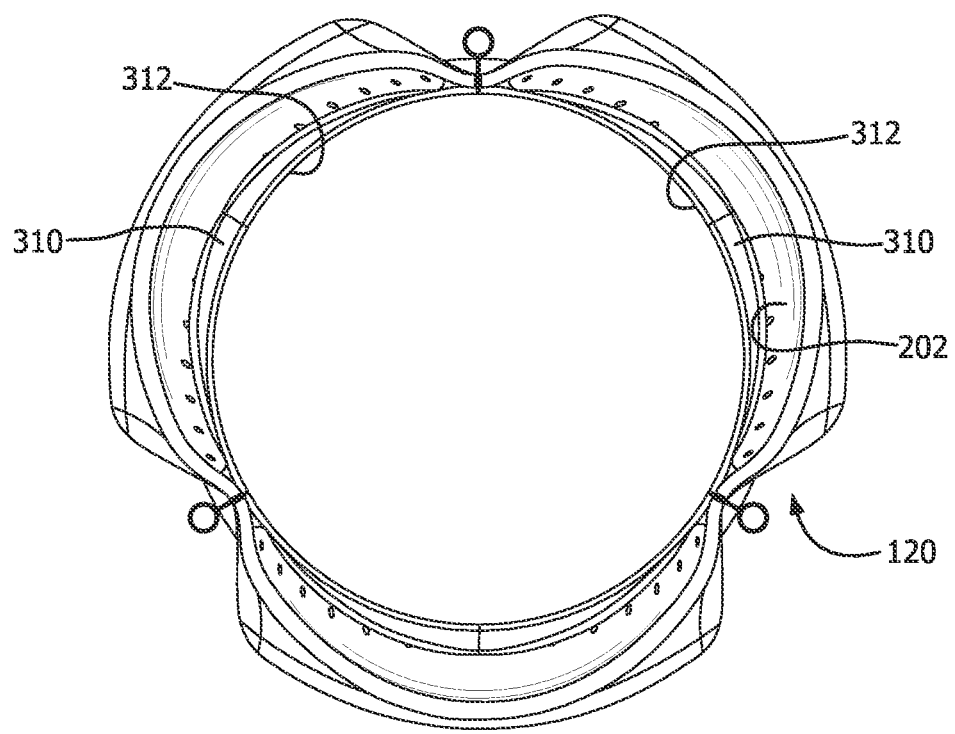
FIG. 1B illustrates an interior downstream view of a valve structure in an open configuration.
Figure 1C:
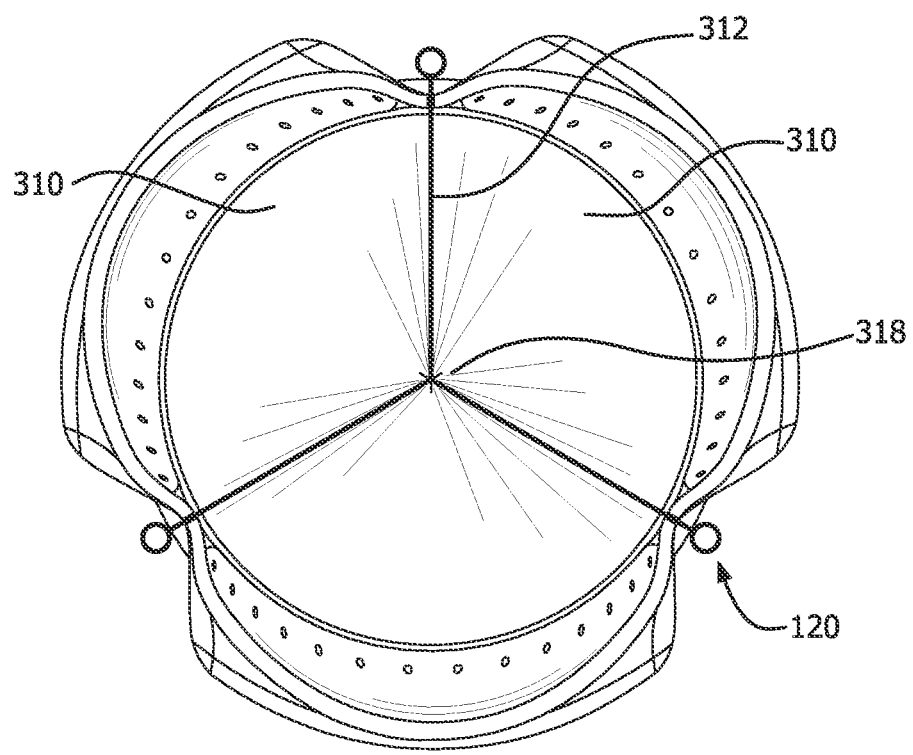
FIG. 1C illustrates an interior downstream view of a valve structure in an closed configuration.

FIGS. 1B and 1C illustrate an interior downstream view of a valve structure 120 in an open configuration, and a closed configuration, respectively. In an open configuration, blood may flow through the valve structure 120, forcing the leaflets 310 towards the conduit inner surface. In a closed configuration the leaflets 310 close toward the center of the conduit lumen 206 with the leaflet free edges 312 coapting with adjacent leaflet free edges 312 which restricts fluid backflow.

The valved conduit 100 that may be used, in a non-limiting example, as a shunt for connecting of the right ventricle to the pulmonary artery following a Norwood operation, as frequently performed for the treatment of hypoplastic left heart syndrome. In one non-limiting example, the valved conduit 100 may be indicated for the correction or reconstruction of the right ventricle outflow tract (RVOT) in pediatric patients. Such reconstruction may be indicated for congenital heart disorders such as tetralogy of Fallot, Truncus Arterious, Dextro-Transposition of the Great Arteries, Pulmonary Atresia of Intact Ventricular Septum, or Aortic Valvular Disease. The valved conduit 100 may also be indicated for the replacement of previously implanted homografts or valved conduits that have become dysfunctional or insufficient. In addition, the valved conduit 100 may have applications in treating a wider range of heart disorders, including other areas of the heart.

Figure 2:
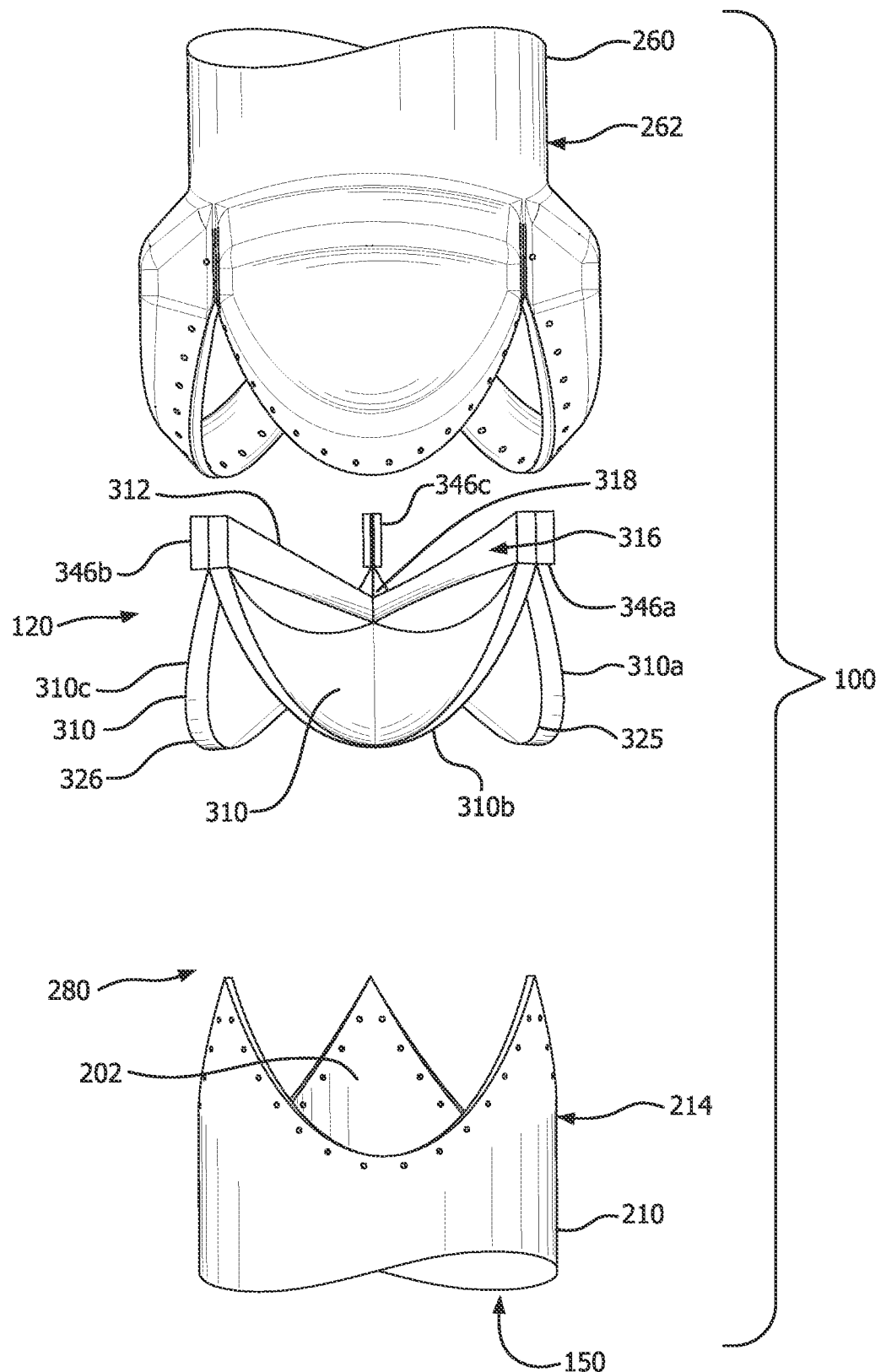
FIG. 2 is an exploded side view of a valved conduit with the leaflets in a closed position, in accordance with an embodiment.
Figure 3:
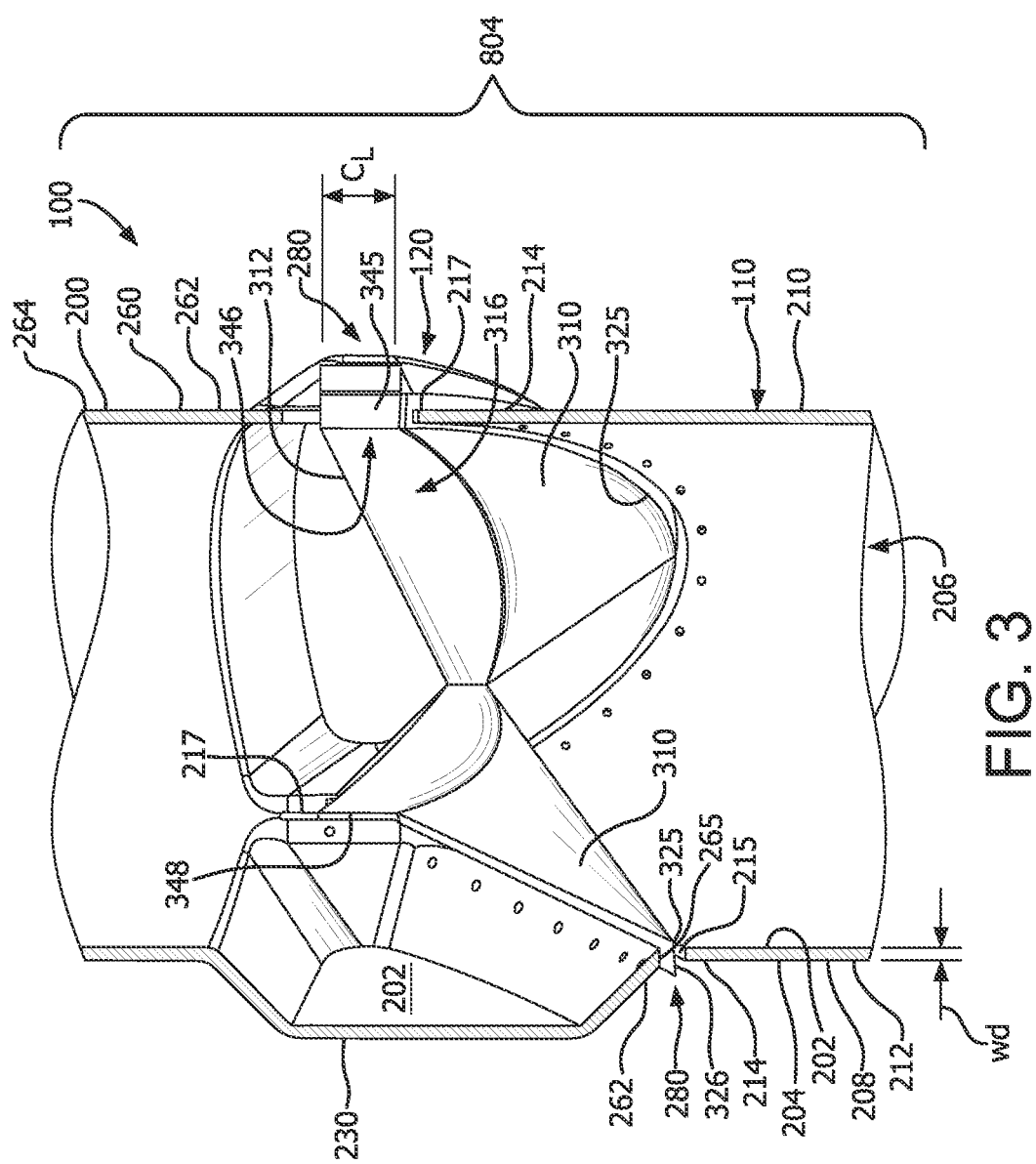
FIG. 3 is a cut-away surface view of a valved conduit with the leaflets in a closed position, in accordance with the embodiment of the valved conduit of FIG. 2.
Figure 4:
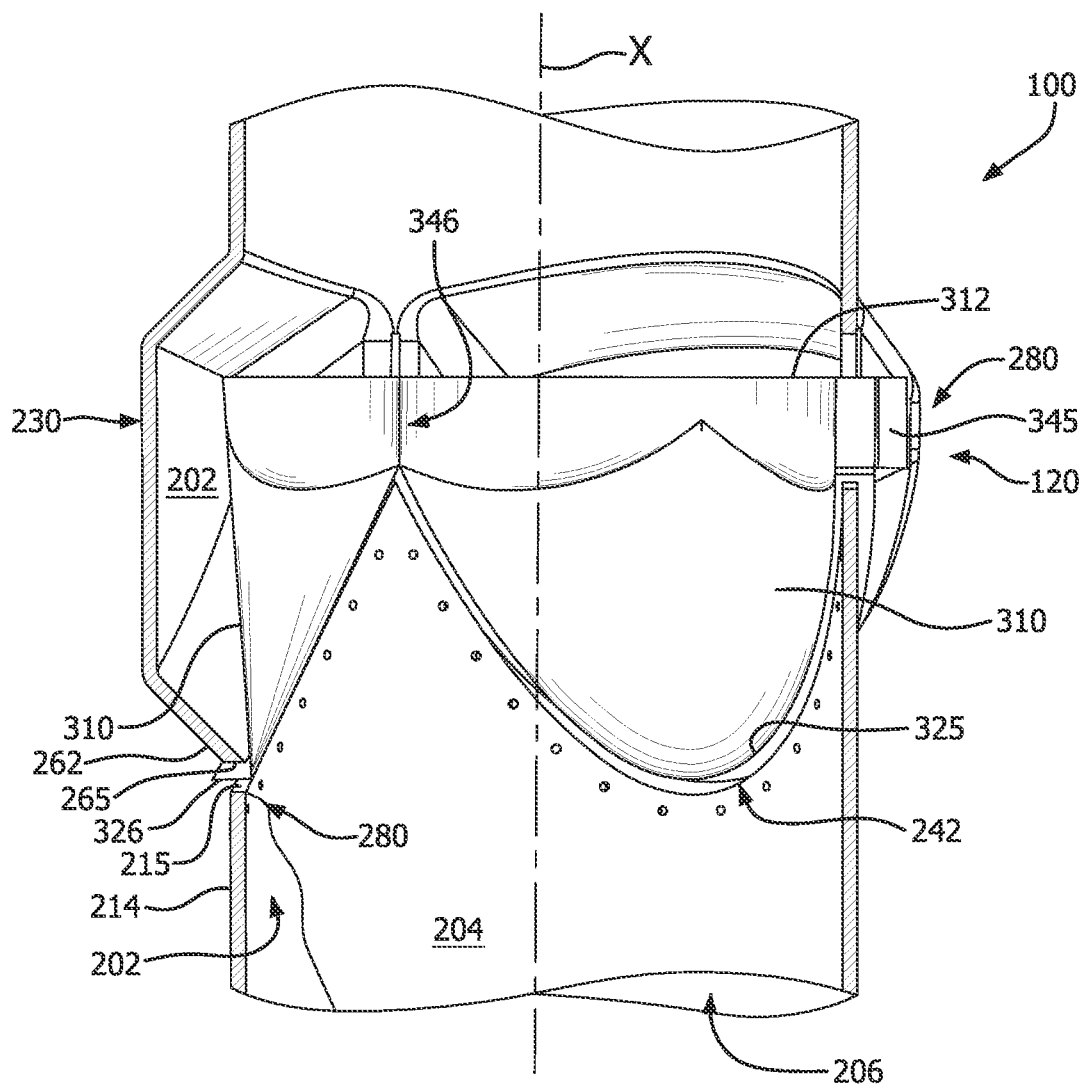
FIG. 4 is a cut-away surface view of a valved conduit with the leaflets in an open position, in accordance with an embodiment of the valved conduit of FIG. 2.

FIGS. 2-5 show various components that are included in the valved conduit 100, in accordance with an embodiment. FIG. 2 is an exploded side view, and FIGS. 3 and 4 are cut-away surface views, respectively, of a valved conduit 100, with the leaflets 310 in a closed and open position, respectively, in accordance with an embodiment. The components of the valved conduit 100 that are visible in FIG. 2 include a valve structure 120 including three leaflets 310 that are flexible. The leaflet free edges 312 of the leaflets 310 come together at a coaptation region 316 in a Y-shaped pattern (when viewed from above) to close the valve structure 120. The valve structure 120 closes in this fashion when the pressure of the blood on the outflow surface is greater than the pressure of the blood on the inflow surface of the valve structure 120. The leaflet free edges 312 of the leaflets 310 move apart to open the valve structure 120 and to let blood flow through the valve structure 120 from the inflow when the pressure of the blood on the inflow surface of the valve structure 120 is greater than the pressure on the outflow surface of the valve structure 120.

The leaflets 310 generally flex about the leaflet base 325 about the junction 280 at the conduit inner surface 202 as the leaflets 310 open and close. In an embodiment, when the valve structure 120 is closed, generally about half of each leaflet free edge 312 abuts an adjacent half of a leaflet free edge 312 of an adjacent leaflet 310, as shown in FIG. 3. The three leaflets 310 of the embodiment of FIG. 2 meet at a triple point 318. The conduit lumen 150 is occluded when the leaflets 310 are in the closed position stopping fluid flow.

In accordance with embodiments, first conduit distal end 214 defines a first conduit joint surface 265 and the second conduit proximal end 262 defines a second conduit joint surface 215 at the junction 280 that is complementary with the first conduit joint surface 265, as shown in FIGS. 3 and 4. In accordance with an embodiment, the first conduit joint surface 265 and the second conduit joint surface 215 are substantially planar and adapted to interface closely together to produce a tight seam when coupled together. In accordance with an embodiment, the first conduit joint surface 265 and the second conduit joint surface 215 are formed by cutting the conduit wall 208 so as to produce the first conduit 210 and the second conduit 260 having complimentary joint surfaces. In accordance with embodiments, the first conduit joint surface 265 and the second conduit joint surface 215 are at an angle to the conduit inner surface 202 such that, when the leaflet attachment edge 326 is coupled therebetween, at least a portion of the leaflet 310 extends from the conduit inner surface 202 in a preferred direction. In accordance with an embodiment, the first conduit joint surface 265 and the second conduit joint surface 215 are perpendicular to the conduit inner surface 202 at the junction 280 such that the leaflets 310 extend perpendicular, or 90 degrees, from the conduit inner surface 202 at the junction 280, as shown in FIG. 3. The leaflets 310 may extend from the commissure slot 217 in a direction perpendicular to the conduit inner surface 202. As such, the leaflets 310 exhibit a bias toward the closed position. This may be beneficial in that the leaflets 310 will tend to close earlier during the phase of the cardiac cycle where the blood is decelerating or reversing. An earlier closure will tend to reduce back flow through the valve structure 120. In accordance with another embodiment, the first conduit joint surface 265 and the second conduit joint surface 215 are-greater than 45 degrees to the conduit inner surface 202 in the downstream direction, excluding the commissure slot 217 which remains perpendicular, such that the leaflets 310 extend at an angle greater than 45 degrees from the conduit inner surface 202 in the downstream direction at the junction 280, such that the leaflets 310 may exhibit a bias toward the closed position. In accordance with another embodiment, the first conduit joint surface 265 and the second conduit joint surface 215 are at an angle to the conduit inner surface 202 in the downstream direction that is at or between an angle of the leaflets in an open position and a closed position such that the leaflets are in a neutral position, that is, biased in a position between fully open and fully closed. The angle may determine, for example, but not limited to, the opening and closing dynamics of the leaflets by imparting a bias on the leaflets.

Figure 5:
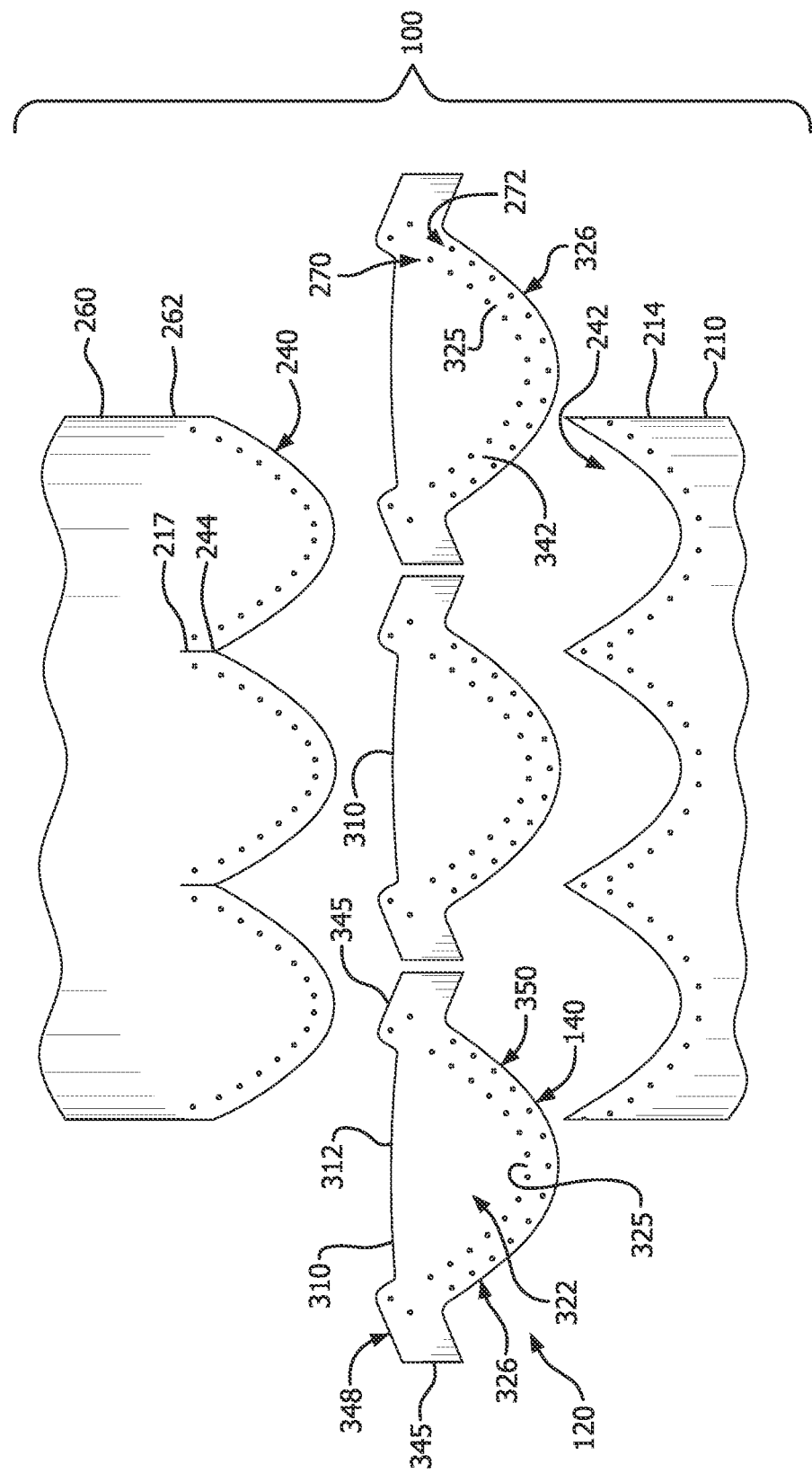
FIG. 5 is an exploded view wherein the annular components have been laid flat, in the case of a tube, longitudinally cut and laid open, so as to better illustrate the elements of the valved conduit of the embodiment of FIG. 2.

FIG. 5 is an exploded view wherein the annular components have been laid flat, in the case of a tube, longitudinally cut and laid open, so as to better illustrate the elements of the valved conduit 100. The valved conduit 100 comprises a first conduit 210, a valve structure 120, and a second conduit 260.

Valve Structure

Figure 6:
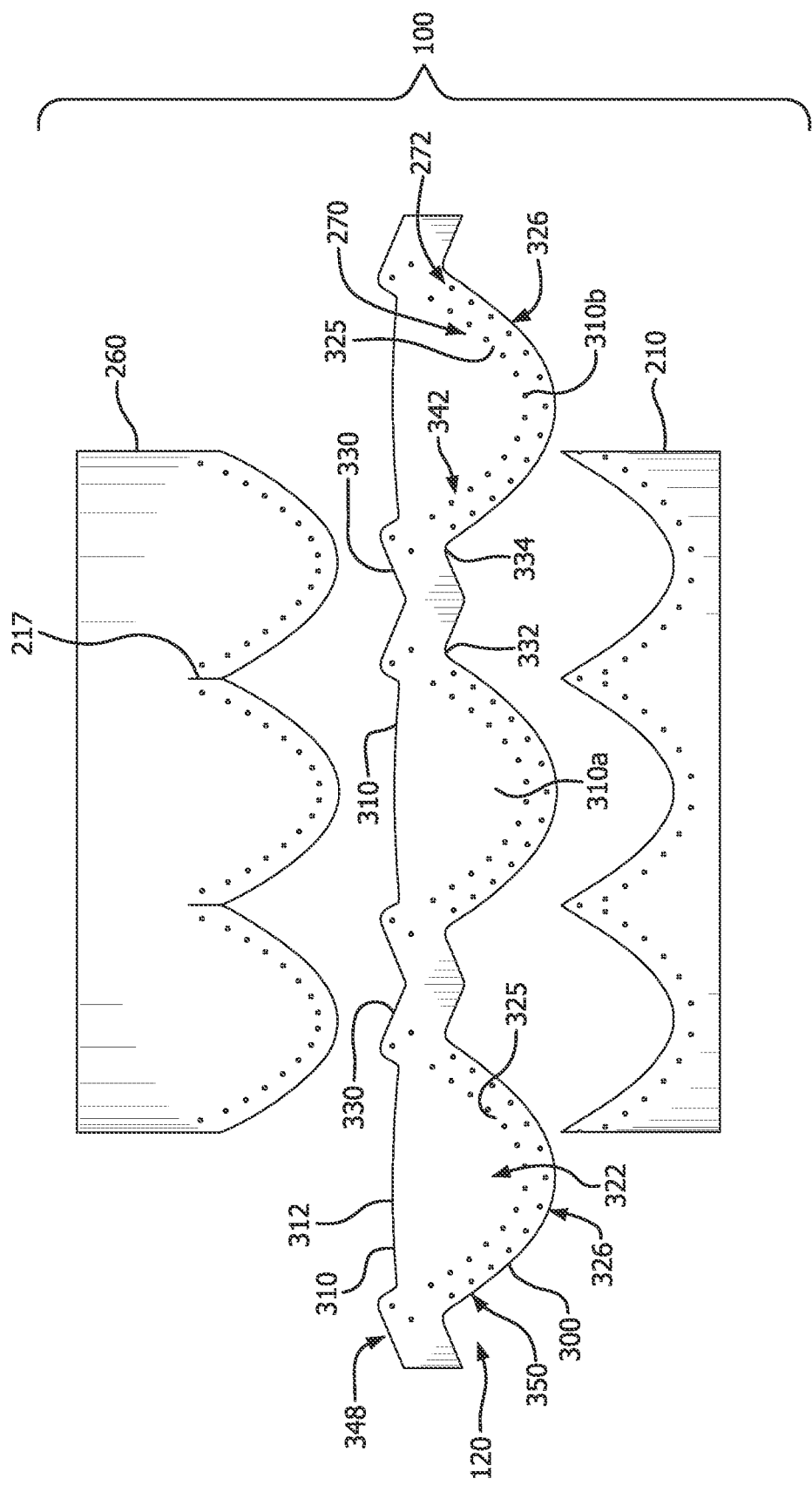
FIG. 6 is an exploded view wherein the annular components have been laid flat, in the case of a tube, longitudinally cut and laid open, so as to better illustrate the elements of the valved conduit of an embodiment were the valve structure is a leaflet construct comprising a plurality of leaflets that are joined together by a bridge region.

The valve structure 120 comprises one or more leaflets 310. In one embodiment, the valve structure 120 is a plurality of leaflets 310 that are separate from each other, as shown in FIG. 5. In another embodiment, the valve structure 120 is a leaflet construct 300 comprising a plurality of leaflets 310 that are joined together by a bridge region 330 between adjacent leaflets 310, as shown in FIG. 6.

Each leaflet 310 is a relatively thin sheet-like element. The material from which a valve structure 120 may be fabricated may have a thickness of about mm to about 0.5 mm. In one embodiment, the valve structure 120 may be cut out of the material by hand, or with a tool, including punch and die-cut tools. In another embodiment, the valve structure 120 may be cut out with a laser-cutter on an automated system for accuracy and repeatability based on a pattern.

Each leaflet 310 has a leaflet free edge 312 and a leaflet attachment edge 326. The portion of the leaflet 310 bound by the leaflet attachment edge 326 and the leaflet free edge 312 is referred to as the leaflet belly 322. The intersection of the leaflet belly 322 and the leaflet attachment edge 326 is referred to as the leaflet base 325. The leaflet attachment edge 326 defines a commissure region 348 adjacent to the leaflet free edge 312. The leaflet attachment edge 326 that does not include the commissure region 348 defines a base attachment edge 350. In the embodiment of FIG. 5 showing separate leaflets 310, the commissure region 348 defines commissure tabs 345. In the embodiment of FIG. 6, the commissure region 348 defines the bridge region 330.

The leaflet attachment edge 326 is operable to be coupled between a first conduit distal end 214 and a second conduit proximal end 262 that are coaxially placed defining a junction 280, as shown in FIGS. 2, 3 and 4. The leaflet base 325 is located directly adjacent the conduit inner surface 202 at the junction 280. The shape of the junction 280 at the conduit inner surface 202 defines, at least in part, the shape of the leaflet base 325. During operation of the valve structure 120, the leaflet 310 will bend at the leaflet base 325.

The leaflet attachment edge 326 of each of the leaflets 310 is extended between the first conduit distal end 214 and the second conduit proximal end 262 and coupled thereto, with, such as, but not limited to, suture, adhesive, thermal bonding, or other means. In accordance with an embodiment, a portion of the leaflet attachment edge 326 extends beyond the conduit outer surface 204.

The length $C_L$ of the commissure region 348 determines, at least in part, the length of the coaptation region 316 between adjacent leaflet free edges 312 in embodiments of the valve structure 120 having more than one leaflet 310. The commissure region 348 is received in and extends through a commissure slot 217 defined by the second conduit proximal end 262 as will be described below.

The leaflet attachment edge 326 at the commissure region 348 of adjacent leaflets 310 meet at a commissure slot 217. The height of the leaflet 310 between the leaflet base 325 and the leaflet free edge 312 is operable such that the leaflet free edge 312 of one leaflet 310 coapts with a leaflet free edge 312 of an adjacent leaflet 310 when in the closed position.

Figure 9A:
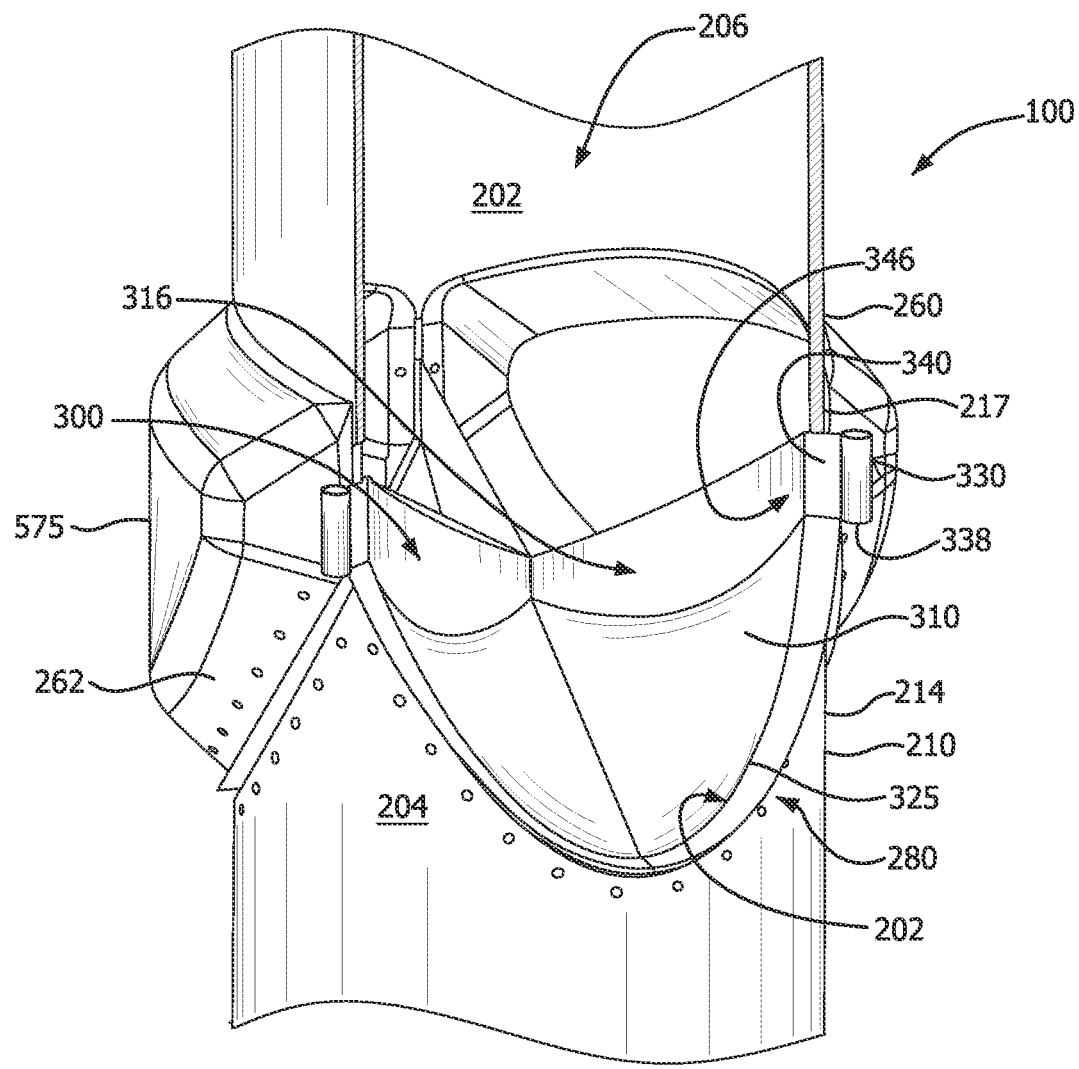
FIG. 9A is a cut-away surface view of a valved conduit showing the valve structure as a leaflet construct in a closed position, in accordance with an embodiment.
Figure 9B:
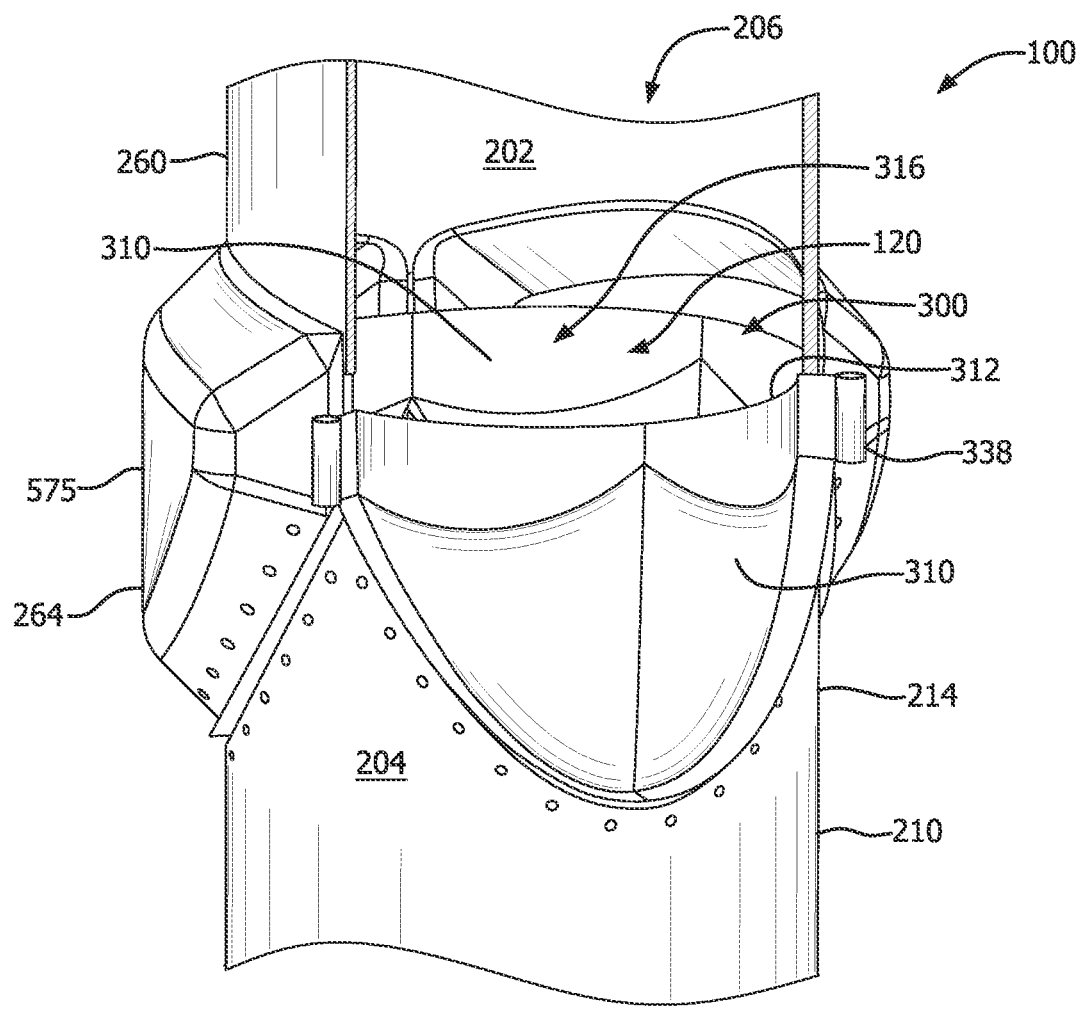
FIG. 9B is a cut-away surface view of a valved conduit showing the valve structure as a leaflet construct in an open position, in accordance with the embodiment of FIG. 9A.

Referring to FIGS. 9A and 9B, as previously discussed, the shape of the leaflet base 325 is determined, at least in part, by the shape of the first conduit distal end 214 and the second conduit proximal end 262 at the conduit inner surface 202 at the junction 280, referred herein as the junction shape. The shape of the leaflet base 325 follows generally the junction shape as it extends into the conduit lumen 206 from the junction 280.

As shown in FIGS. 2 and 5, the first conduit distal end 214 defines a plurality of conduit parabolic valleys 242, and the second conduit proximal end 262 defines a plurality of complementary conduit parabolic hills 240. The leaflet attachment edge 326 defines complementary leaflet parabolic hills 140 to generally conform to the junction shape and, in an embodiment, extend from the junction 280 at the conduit outer surface 204 when disposed within the junction 280, as shown in FIG. 4. The leaflets 310 are sheet-like, relatively thin and flexible and thus take on the shape of the conduit parabolic valleys 242 and the complimentary conduit parabolic hills 240, and, in operation, will bend at the junction 280 adjacent the conduit inner surface 202, thus defining the leaflet base 325.

Figure 7:
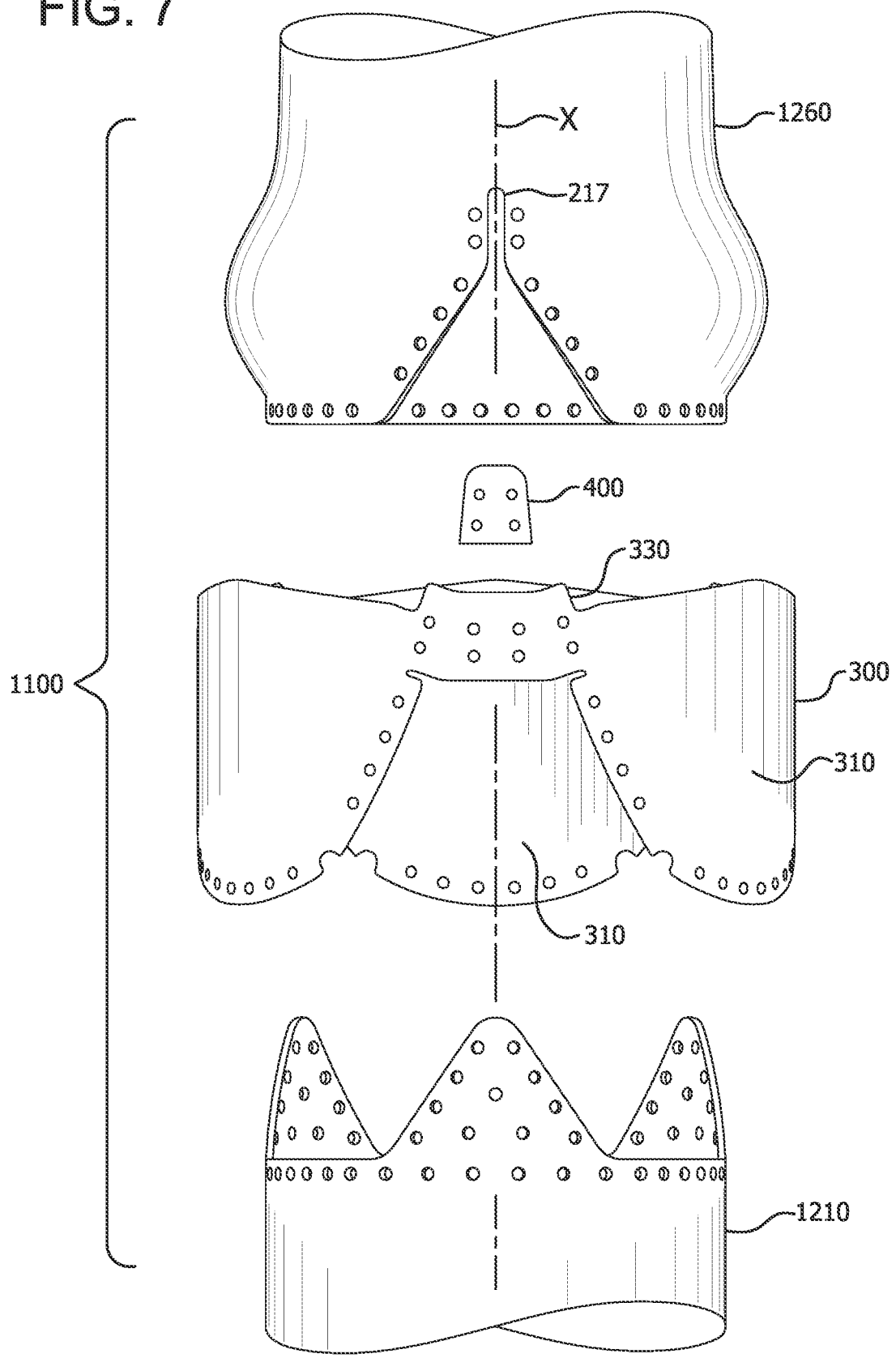
FIG. 7 is a side, exploded view of an embodiment of a valved conduit.

FIG. 7 is a side, exploded view of an embodiment of a valved conduit 1100, and FIG. 8 is a representation of the embodiment of FIG. 7 laid flat, in the case of a tube, longitudinally cut and laid open to a flat orientation so as to better illustrate the elements. Each leaflet 310, at the leaflet attachment edge 326, has substantially the shape of an isosceles trapezoid having two leaflet sides 314, a leaflet base 325 and a leaflet free edge 312 opposite the leaflet base 325, corresponding to the two leaflet attachment sides 223 and a leaflet attachment base 225 defined in the first conduit distal end 214. The two leaflet sides 314 diverge from the leaflet base 325, wherein the leaflet base 325 is substantially flat.

Figure 11:
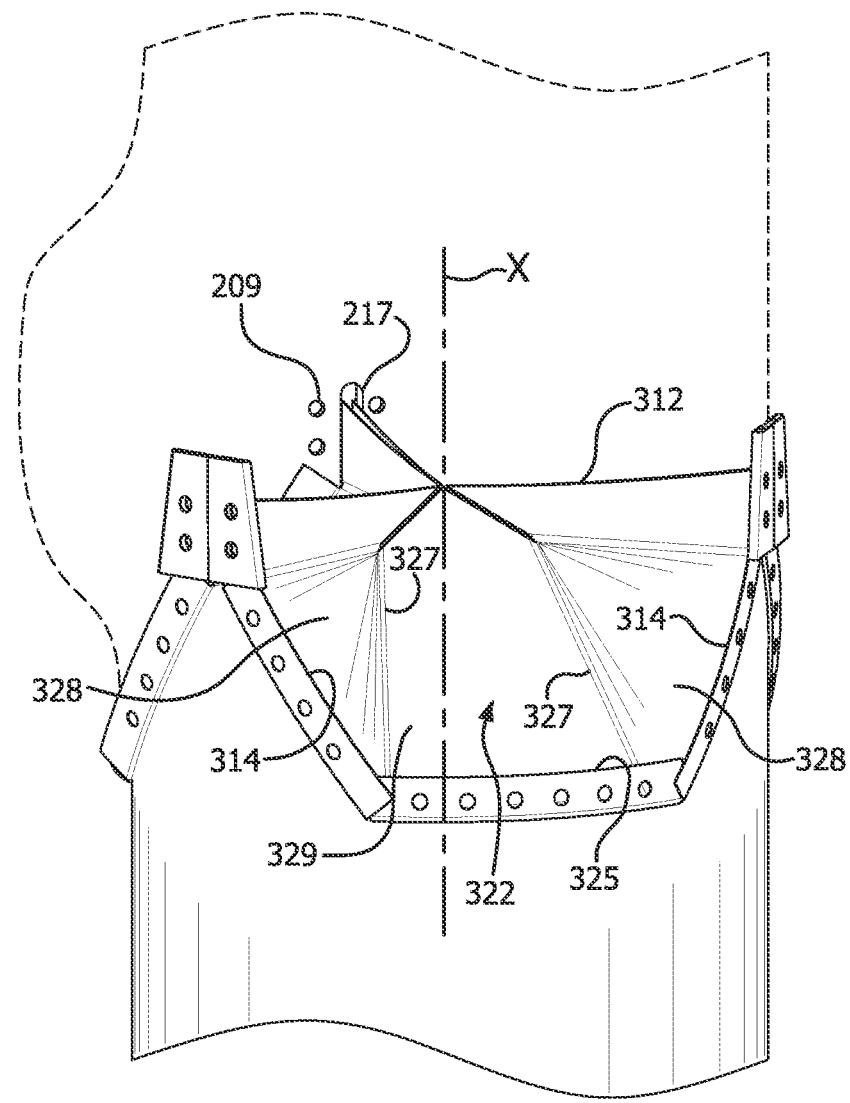
FIG. 11 is a side, partially cut-away view of an embodiment of the valve structure as a leaflet construct including a plurality of leaflets.

As shown in FIG. 11, in accordance with other embodiments of the valved conduit 100, each leaflet belly 322 includes a belly central region 329 and two belly side regions 328 on opposite sides of the belly central region 329. The belly central region 329 is defined by a shape substantially that of an isosceles trapezoid defined by two belly central region sides 327, the leaflet base 325 and the leaflet free edge 312. Each of the belly side regions 328 has a shape substantially that of a triangle and each are defined by one of the belly central region sides 327, one of the leaflet sides 314, and the leaflet free edge 312.

The isosceles trapezoid shape of the leaflet base 325 will produce a different leaflet bending character as compared with a parabolic shape. The bending characteristics of a leaflet base 325 that has a belly base 324 that is flat as provided by the isosceles trapezoid shape will produce a flat hinge-like bending at the leaflet base 325 that may prevent bulking and wrinkling during operation as compared with a rounded leaflet base 325.

As shown in FIG. 5, each of the leaflets 310 have a leaflet belly 322, and a leaflet attachment edge 326. The leaflet belly 322 of each leaflet 310 is the operating portion of the leaflet 310 when in a finished and implanted valved conduit 100. The leaflet attachment edge 326 of each leaflet 310 is the portion that is used to secure the leaflet 310 to the junction 280.

As previously discussed, the shape of the leaflet 310 is defined, at least in part by the shape of the first conduit distal end 214 and the leaflet free edge 312. The shape of the leaflets 310 can also be defined, at least in part, by the materials and processes used to manufacture the leaflet 310, such as, but not limited, those described below. For example, in accordance with an embodiment, the shape of the leaflet 310 also depends in part on molding the leaflets 310 using molding and trimming processes to impart a predetermined shape to the leaflet 310.

It is appreciated that the valve structure 120 with either separate leaflets or a leaflet construct 300 may be composed of any number of leaflets 310. FIG. 2 illustrates one non-limiting example of a multi-leaflet valve structure 120 composed of three leaflets 310. It is understood that a valve structure 120 may be composed of any number of leaflets 310. For example, a valve structure 120 having four leaflets 310 may also be considered. In FIG. 2, a three-leaflet valve structure 120 comprises three leaflets 310, each leaflet 310 having a leaflet attachment edge 326 and a leaflet free edge 312. Such a three-leaflet valve structure 120 includes three commissures 346: a first commissure 346a between a first leaflet 310a and a second leaflet 310b, a second commissure 348b between the second leaflet 310b and a third leaflet 310c and a third commissure 346c between the third leaflet 310c and the first leaflet 310a. Each commissure 346 may have a commissure length $C_L$ as shown in FIG. 3.

Leaflet Construct

In one embodiment, the valve structure 120 comprises a plurality of separate leaflets. In another embodiment, the valve structure 120 comprises a leaflet construct 300 including a plurality of leaflets 310.

With reference to FIG. 6, in accordance with an embodiment, the leaflet construct 300 defines a contiguous annular ring defining a plurality of leaflets 310 with a commissure region 348 in the form of a bridge region 330 between each of the leaflets 310, as shown in FIG. 6, and also as shown in FIG. 7 for a slightly different embodiment. As used herein, contiguous means without a break or a seam, that is, seamless. Each bridge region 330 defines a bridge first end 332 adjacent a first leaflet 310a and a bridge second end 334 adjacent a second leaflet 310b. The leaflets 310 extend radially inward in the conduit lumen 206 when coupled to the conduit 200. Each of the leaflets 310 define a leaflet attachment edge 326 that is operable to extend into the junction 280 between the first conduit distal end 214 and a second conduit proximal end 262.

With reference to FIG. 6, in accordance with another embodiment, the leaflet construct 300 defines a flat sheet that is subsequently formed into an annular ring defining a plurality of leaflets 310 with a commissure region 348 in the form of a bridge region 330 between each of the leaflets 310, as shown in FIG. 6, and also as shown in FIG. 7 for a slightly different embodiment. In this embodiment, there will be a seam where the sheet is formed into a tube with the edges coupled together. Each bridge region 330 defines a bridge first end 332 adjacent a first leaflet 310a and a bridge second end 334 adjacent a second leaflet 310b. The leaflets 310 extend radially inward in the conduit lumen 206 when coupled to the conduit 200. Each of the leaflets 310 define a leaflet attachment edge 326 that is operable to extend into the junction 280 between the first conduit distal end 214 and a second conduit proximal end 262.

Figure 10:
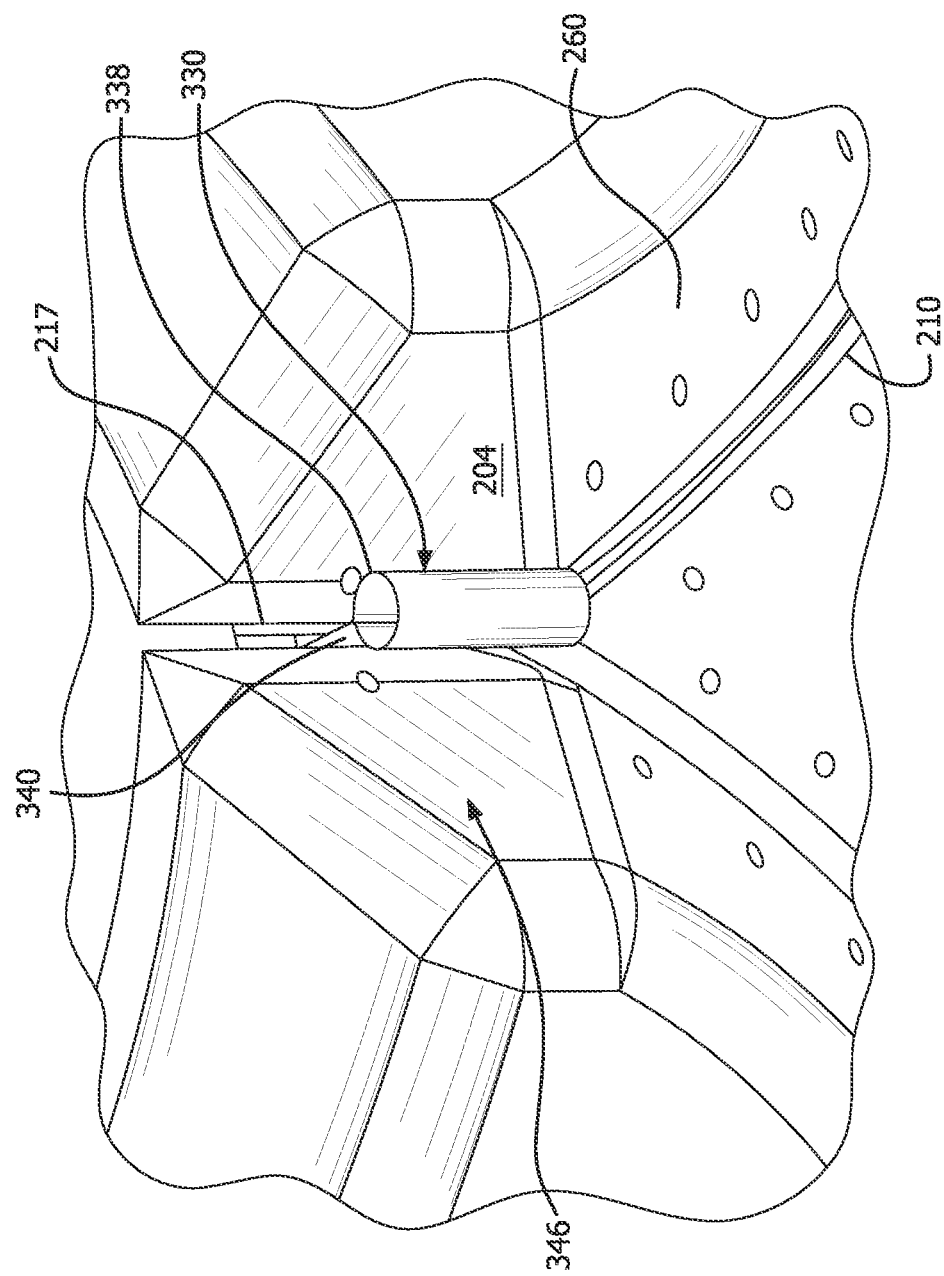
FIG. 10 is a close-up of the commissure showing the bridge loop of the embodiment of FIG. 9A.

FIGS. 9A and 9B are cut-away surface views of a valved conduit 100 showing the valve structure 120 as a leaflet construct 300 in a closed and open position, respectively, in accordance with an embodiment. FIG. 10 is a close-up of the commissure 346 showing the bridge loop 338 of the embodiment of FIGS. 9A and 9B. Each of the bridge regions 330 may be folded so as to define a bridge loop 338 with a coaptation neck 340 between the bridge loop 338 and the adjacent leaflets 310. The coaptation neck 340 is operable to pass through one of the commissure slots 217 so that the bridge loop 338 is adjacent to the conduit outer surface 204 and the leaflets 310 extend radially inward from the conduit inner surface 202, as shown in FIGS. 9A and 9B when in the closed position.

One leaflet 310 may be essentially mirror-image symmetric with respect to the commissure 346.

The leaflet construct 300 can be made of polymer. For example, pre-shaped polymer leaflets can be made by starting from a cylinder of polymer material and cutting into a shape like that shown in FIGS. 6, 7 and 8.

The leaflet construct 300 can also be made from a flat sheet of a material, such as, but not limited to, a polymer material, that has been cut into a shape like that shown in FIGS. 6 and 8 and subsequently coupled together into an annular shape, as shown in FIG. 7. A leaflet construct 300 having a seam, though, may not have the advantages of a contiguous, seamless construct that may exhibit a higher tensile strength characteristics at the commissure 346. The advantages provided by a retention element 400 inside the bridge loop 338 may still be realized in embodiments where a retention element 400 is used, as will be discussed below. It is understood that the leaflet construct 300 may be cut from a material that is formed or has been formed into any suitable form for the particular purpose.

Another way that the leaflet construct 300 may be formed, assuming the use of a material for the leaflets that is suitable for formation in this way, is by compression or injection molding.

Figure 12:
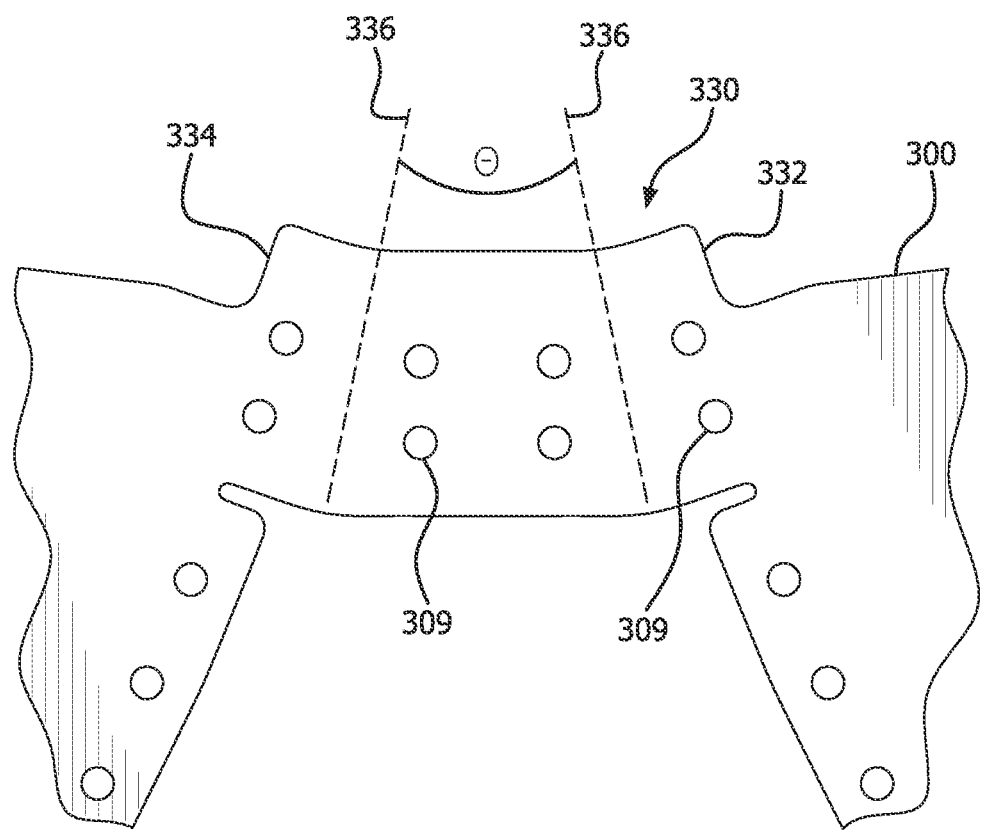
FIG. 12 is a close front view of the bridge region, in accordance with an embodiment.

Between each of the leaflets 310 is a bridge region 330, as shown in FIGS. 6-9. The bridge region 330 is operable to extend through the commissure slot 217 such that a portion of the bridge region 330 extends away from the conduit outer surface 204. In accordance with an embodiment, the bridge region 330 is operable to be formed into a bridge loop 338, folding about two loop fold lines 336 so as to contain a retention element 400 therein as discussed below, as shown in FIGS. 7, 8, and 11. Due to the curvature of the conduit outer surface 204 as the commissure 346, the two loop fold lines 336 form an angle alpha, which corresponds to retention element surfaces 402 as shown in FIG. 12, in accordance with an embodiment.

Leaflet and Leaflet Construct Material

In accordance with an embodiment, the valve structure 120, whether the separate leaflets 310 or the leaflet construct 300 can comprise a biocompatible material. In accordance with an embodiment, the biocompatible material that makes up the valve structure 120 comprises a biological material, such as, but not limited to, bovine pericardium.

In accordance with an embodiment, the valve structure 120, whether the separate leaflets 310 or the leaflet construct 300 can comprise a biocompatible material that is not of a biological source and that is sufficiently compliant and strong for the particular purpose, such as a biocompatible polymer. In an embodiment, the valve structure 120 comprises a membrane that is combined with an elastomer, such as by imbibing, to form a composite material.

The leaflet 310 and leaflet construct 300 can comprise, according to an embodiment, a composite material comprising an expanded fluoropolymer membrane, which comprises a plurality of spaces within a matrix of fibrils, and an elastomeric material. It should be appreciated that multiple types of fluoropolymer membranes and multiple types of elastomeric materials can be combined to form a composite material while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, can comprise a PTFE homopolymer. In alternative embodiments, blends of PTFE, expandable modified PTFE and/or expanded copolymers of PTFE can be used. Non-limiting examples of suitable fluoropolymer materials are described in, for example, U.S. Pat. No. 5,708,44, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,50, to Xu et al.

The expanded fluoropolymer membrane can comprise any suitable microstructure, such as pores, for achieving the desired leaflet performance. Other biocompatible polymers which can be suitable for use in leaflet include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

Further examples of leaflet and leaflet construct materials include: wherein the leaflet and leaflet construct comprises at least one fluoropolymer membrane layer; wherein the leaflet and leaflet construct comprises a laminate having more than one fluoropolymer membrane layer; wherein the at least one fluoropolymer membrane layer is an expanded fluoropolymer membrane layer; wherein an elastomer is contained within the expanded fluoropolymer membrane layer; wherein the elastomer comprises perfluoromethyl vinyl ether and tetrafluoroethylene; wherein the expanded fluoropolymer membrane layer comprises ePTFE; wherein the leaflet and leaflet construct comprises a composite material having at least one fluoropolymer membrane layer having a plurality of pores and an elastomer present in the pores of at least one of the fluoropolymer membrane layers; wherein the composite material comprises fluoropolymer membrane by weight in a range of about 10% to 90%; wherein the elastomer comprises (per)fluoroalkylvinylethers (PAVE); wherein the elastomer comprises a copolymer of tetrafluoroethylene and perfluoromethyl vinyl ether; wherein the elastomer is silicone; wherein the elastomer is a fluoroelastomer; wherein the elastomer is a urethane; and wherein the elastomer is a TFE/PMVE copolymer; wherein the TFE/PMVE copolymer comprises essentially of between about 40 and 80 weight percent perfluoromethyl vinyl ether and complementally 60 and 20 weight percent tetrafluoroethylene; and wherein the leaflet and leaflet construct comprises silicone.

Conduit

As previously discussed, in accordance with the embodiment of FIG. 3, the valved conduit 100 includes a conduit 200 and a valve structure 120 incorporated into the conduit 200. The conduit 200 is generally tubular and flexible. The conduit 200 has a conduit wall 208 defining a conduit outer surface 204 defining an outer diameter (OD) and a conduit lumen 206 defining a conduit inner surface 202 having an inner diameter (ID). The wall 208 has a thickness Wd. In an embodiment, the conduit 200 has an ID that is less than 10 mm. In another embodiment, the conduit 200 has an ID that is greater than 10 mm but less than 25 mm. In yet another embodiment, the conduit 200 has an ID that is greater than 25 mm.

The conduit 200 comprises a first conduit 210 and a second conduit 260 that are joined at a junction 280 with the valve structure 120 extending between and therefrom, as will be discussed below. The first conduit 210 has a first conduit proximal end 212 and a first conduit distal end 214 opposite the first conduit proximal end 212. The second conduit 200 has a second conduit proximal end 262 and a second conduit distal end 264 opposite the second conduit proximal end 262. The first conduit distal end 214 has a complementary shape to the second conduit proximal end 262 such that the first conduit distal end 214 may be matched up and coupled to the second conduit proximal end 262 at a junction 280.

In an embodiment, the second conduit proximal end 262 defines the shape, size and/or dimensions as the desired shape of the leaflet base 325 of the leaflet 310. The first conduit distal end 214 defines a complementary shape, size and/or dimensions so as to conform to and closely fit the shape of the second conduit proximal end 262. The thickness of the leaflet attachment edge 326 is relatively thin and will not obstruct the fit between the first conduit distal end 214 and the second conduit proximal end 262.

In accordance with an embodiment, the first conduit 210 and the second conduit 260 are formed by cutting a length of conduit 200 into two lengths about a cut line, wherein the cut line proscribes the desired complementary shape of the first conduit distal end 214 and the second conduit proximal end 262. As will be described later, the first conduit distal end 214 is reattached with the valve structure 120 therebetween.

Wherein the first conduit distal end 214 defines a plurality of conduit parabolic valleys 242, and wherein the second conduit proximal end 262 defines a plurality of complementary conduit parabolic hills 240, as shown in FIG. 5. At the conduit hill base 244 of the conduit parabolic hills 240 and between each conduit parabolic hill 240 extends a commissure slot 217. The commissure slot 217 is operable to receive either the commissure tabs 345 or bridge loop 338 there through. Each commissure slot 217 extends through the wall thickness and is aligned parallel to the axis X, the longitudinal axis of the conduit, in accordance with an embodiment.

In one embodiment, the conduit 200 may have a wall thickness of about 0.1 mm to about 1.5 mm. In another embodiment, the conduit 200 may also have an inner diameter of about 6 mm to about 28 mm. It is appreciated that a wall thickness and diameter may be smaller or larger suitable for the particular purpose.

In accordance with an embodiment, the conduit 200 may further comprise a conduit sinus 230 in the second conduit proximal end 262 which is adjacent one or more of the leaflets 310 adjacent to the leaflet base 325, as shown in FIGS. 2-4.

Conduit sinuses 230 may be generally concave with respect to the conduit inner surface 202 of the conduit 200. In one non-limiting example, conduit sinuses 230 may be generally spheroidal concave. In another non-limiting example, conduit sinuses 230 may be generally cubically concave. It may be understood that the outline and cross section of conduit sinuses 230 may have any geometry as long as the conduit sinuses 230 maintain a concavity with respect to a conduit inner surface 202.

Again, FIG. 3 is a side view of an embodiment of the valve structure 120 in a closed configuration, and FIG. 4 is a side view of an embodiment of the valve structure 120 in an open configuration. In the open configuration the leaflets 310 are disposed in an extended downstream-pointing position. An interior concavity of each of the conduit sinuses 230 is shown. In the closed configuration, each leaflet 310 is disposed in a neutral position. In the neutral position, the leaflets 310 are disposed with respect to each other such that their respective leaflet free edges coapt so as to completely occlude the conduit lumen 206.

The one or more conduit sinuses 230 may be formed into the conduit according to any method appropriate for deforming the conduit wall 208. Examples of conduit wall 208 deformation methods may include, without limitation, one or more of mechanical deformation (such as stretching or mechanical forming), heat forming, and/or vacuum forming. A conduit sinus method may deform the conduit material from the inside of a conduit via applied pressure and/or heat.

In accordance with an embodiment, the material of the conduit 200 at the rigidified region 804, including the conduit sinuses 230, is densified and/or rigidified such that the conduit sinuses 230 and the junction 280 retain their shape during handling and use. Densification refers, in general, and specifically to ePTFE conduit, to a process of selectively making the material more dense at selected locations, such as by heating and pressure. For ePTFE material that may be relatively porous, the densification process will reduce porosity and make the area more rigid.

Wherein the conduit 200 outside of the rigidified region 804 is rather flexible, the conduit 200 at the rigidified region 804 is made to be more rigid so as to support the circular shape of the conduit lumen 206 at the junction 280 as well as better retain the shape of the sinuses 575. Deformation at the junction 280 might result in the valve structure 120 not operating properly. The rigidified region 804 of the conduit 200 provides radial compressive strength while the conduit outer surface 204 is atraumatic to adjacent tissue. The rigidified region 804 also assists in better accuracy for cutting the parting line 802, shown in FIG. 17, as discussed below, as well as creation and placement of the first conduit apertures 219 and second conduit apertures 269, also assisting in the use of automated manufacturing equipment.

Assembly

The first conduit distal end 214 and the second conduit proximal end 262 are coupled together with the leaflet attachment edge 326 therebetween with any suitable process, in accordance with embodiments. Processes involving adhesive, heat welding, bonding, and suturing are anticipated.

In an embodiment, illustrated in FIG. 2, the valve structure 120 comprise a plurality of separate leaflets 310. Each leaflet 310 is separately affixed at the junction 280 of a conduit 200. The leaflet attachment edge 326 of each leaflet 310 is disposed between the first conduit distal end 214 and the second conduit proximal end 262 as shown in FIG. 3.

In another embodiment, illustrated in FIG. 11, the valve structure 120 comprise a leaflet construct 300 including a plurality of leaflets 310. The leaflet construct 300 is affixed at the junction 280 of a conduit 200 as a unit. The leaflet attachment edge 326 of each leaflet 310 is disposed between the first conduit distal end 214 and the second conduit proximal end 262.

In accordance with an embodiment, the leaflet attachment edge 326 extends from the junction 280 to adjacent the conduit outer surface 204. In accordance with another embodiment, the portion of the leaflet attachment edge 326 that extends from the junction 280 to adjacent the conduit outer surface 204 is coupled to the conduit outer surface 204.

Leaflet Apertures and Suture

The first conduit distal end 214 and the second conduit proximal end 262 are coupled together with the leaflet attachment edge 326 therebetween with suture 700, in accordance with an embodiment.

As shown in FIG. 5, in accordance with an embodiment, the leaflet attachment edge 326 further comprises a leaflet aperture inner row 270 of a plurality of leaflet apertures 342 collocated with the leaflet base 325 and spaced apart from a leaflet aperture outer row 272 of a plurality of leaflet apertures. The distance between the leaflet aperture inner row 270 and the leaflet aperture outer row 272 corresponds to the thickness Wd of the conduit wall 208, as shown in FIG. 3, where the leaflet attachment edge 326 is placed therebetween at the junction 280. The leaflet apertures 342 of the leaflet aperture inner row 270 are operable to allow passage of suture 700 therethrough adjacent the conduit inner surface 202, and the leaflet apertures 342 of the leaflet aperture outer row 272 are operable to allow passage of suture 700 therethrough adjacent the conduit outer surface 204. The leaflet apertures 342 of the leaflet aperture inner row 270 are in staggered relationship with the leaflet apertures 342 of the leaflet aperture outer row 272, so as to allow a zig-zag suture path, known in the art as a whip stich pattern. Also, the staggered relationship allows for more leaflet material between adjacent leaflet apertures 342 of the leaflet aperture inner row 270 and the leaflet aperture outer row 272 for greater strength of the leaflet attachment edge 326.

It is understood that a number of stich patterns may be used. In accordance with another embodiment, the leaflet apertures 342 of the leaflet aperture inner row 270 are in aligned relationship with the leaflet apertures 342 of the leaflet aperture outer row 272, so as to allow an in-line suture path, known in the art as a blanket stich pattern. The in-line relationship may allow for a more efficient tightening and better retention of the alignment of the seam.

Figure 14:
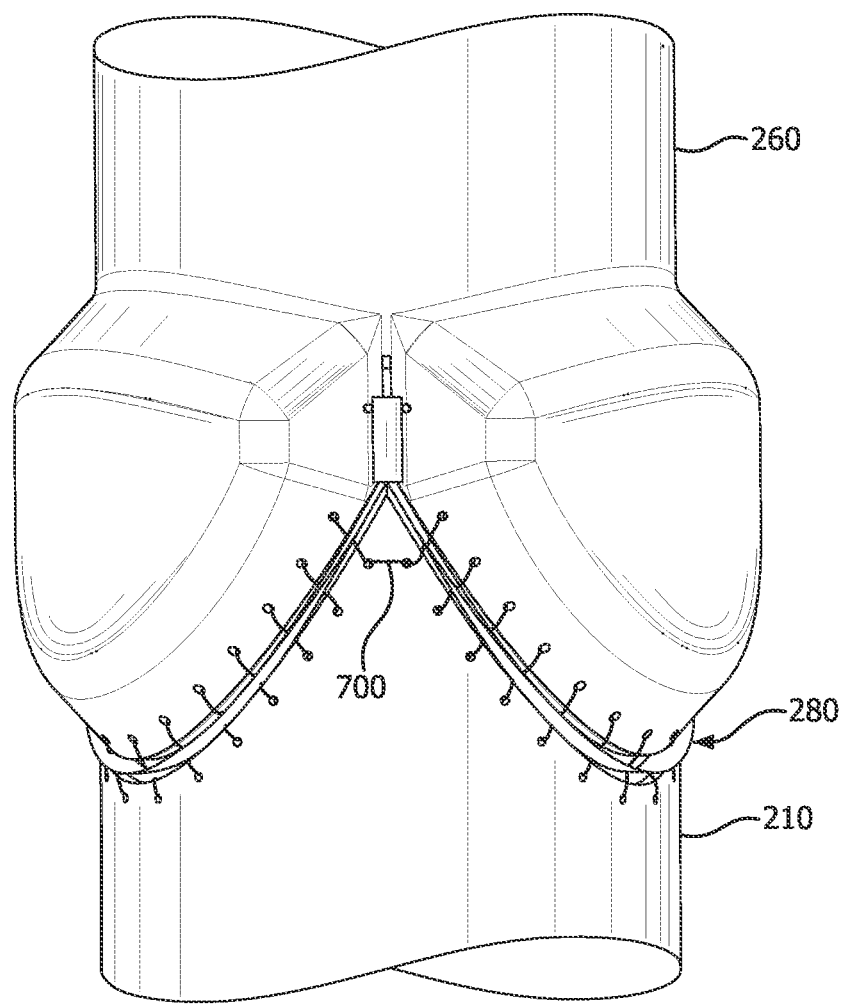
FIG. 14 is a side view of a valved conduit coupled using suture at the junction, in accordance with an embodiment.

The leaflet attachment edge 326 is placed between the facing first conduit distal end 214 and the second conduit proximal end 262 with the conduit wall 208 positioned between the leaflet aperture inner row 270 and the leaflet aperture outer row 272 of the leaflet apertures 342. Suture 700 is passed from the first conduit outer surface 224 through one of the first conduit apertures 219 to the conduit inner surface, extending along the conduit inner surface 202 then passed through an adjacent leaflet aperture 342 of the leaflet aperture inner row 270, and extending along the conduit inner surface 202 then passed through an adjacent second conduit aperture 282 to the conduit outer surface 204, extending along the conduit outer surface 204, then passed through an adjacent leaflet aperture 342 of the leaflet aperture outer row 272, and along the conduit outer surface 204 to the next adjacent first conduit aperture 219 and so forth progressing along the respective rows of apertures, and thus coupling the first conduit distal end 214 and the second conduit proximal end 262 together with the leaflet attachment edge 326 therebetween, as shown in FIG. 14.

The first conduit 210 and the second conduit 260 are joined at the junction 280 with the valve structure 120 extending between and therefrom, with the leaflets 310 extending into the conduit lumen 206 and the leaflet attachment edge 326 extending into the junction 280. In accordance with an embodiment, the leaflet attachment edge 326 extends from the junction 280 to adjacent the conduit outer surface 204. In accordance with another embodiment, a portion of the leaflet attachment edge 326 that extends from the junction 280 to adjacent the conduit outer surface 204 is coupled to the conduit outer surface 204.

In accordance with an embodiment, only one row of leaflet apertures 342 is provided in the leaflet attachment edge 326, as shown in FIG. 7. In accordance with an embodiment, the one row of leaflet apertures 342 is the leaflet aperture inner row 270 which is coupled to the junction 280 with suture 700 passed along the conduit inner surface 202. In accordance with an embodiment, the one row of leaflet apertures 342 is the leaflet aperture outer row 272 which is coupled to the junction 280 with suture 700 passing along the conduit outer surface 204.

In accordance with embodiments, after the junction 280 is coupled, a curable sealant is applied to the junction 280 adjacent the conduit outer surface 204 which may improve coupling strength and prevent leakage at the junction 280.

In any case, the leaflet 310 is not coupled to the conduit inner surface 202 of the conduit 200 but extends through the conduit wall 208 extending from the junction 280 into the conduit lumen 206 of the conduit 200.

Retention Element

Figure 13B:
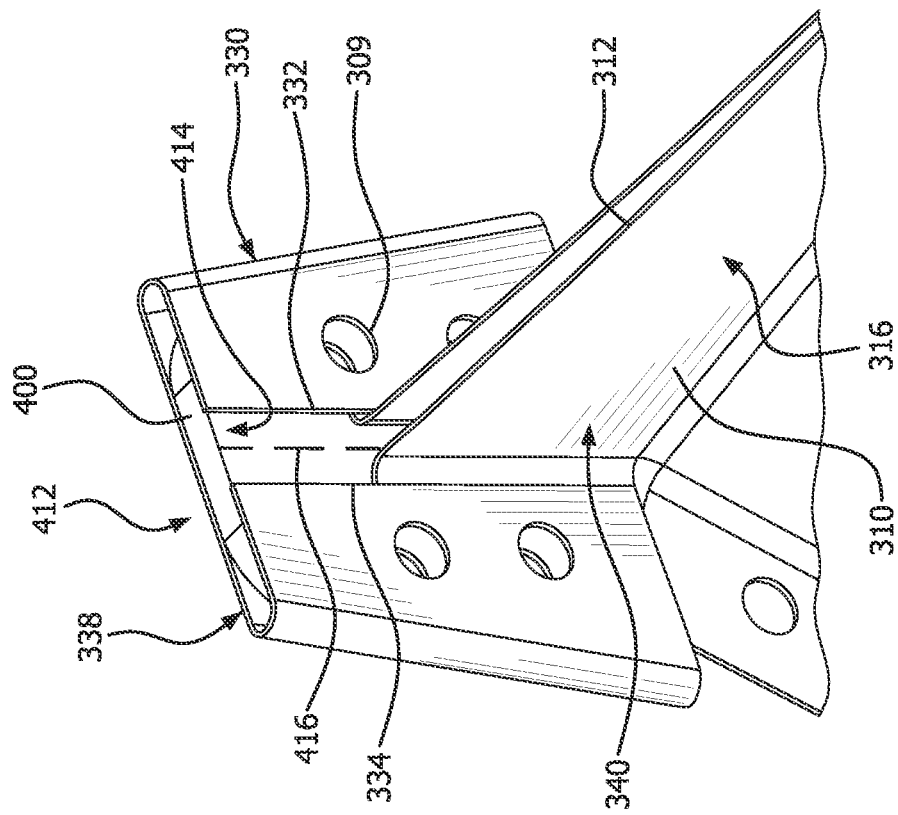
FIG. 13B is a close-up perspective view of the bridge region with a retention element in accordance with the embodiment of FIG. 13A.
Figure 13A:
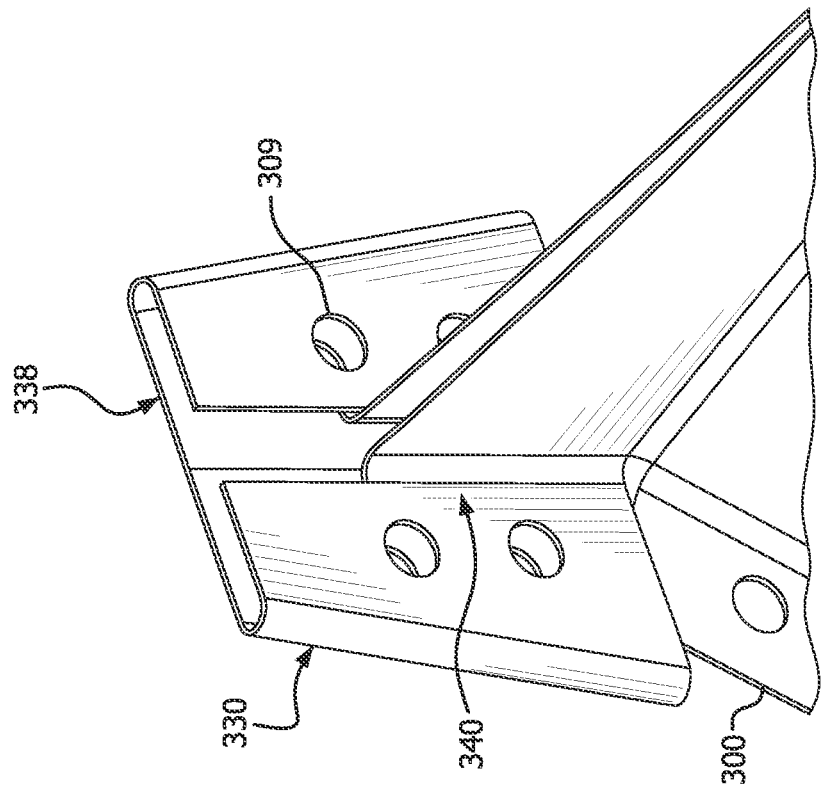
FIG. 13A is a close-up perspective view of the bridge region in accordance with an embodiment.
Figure 13C:
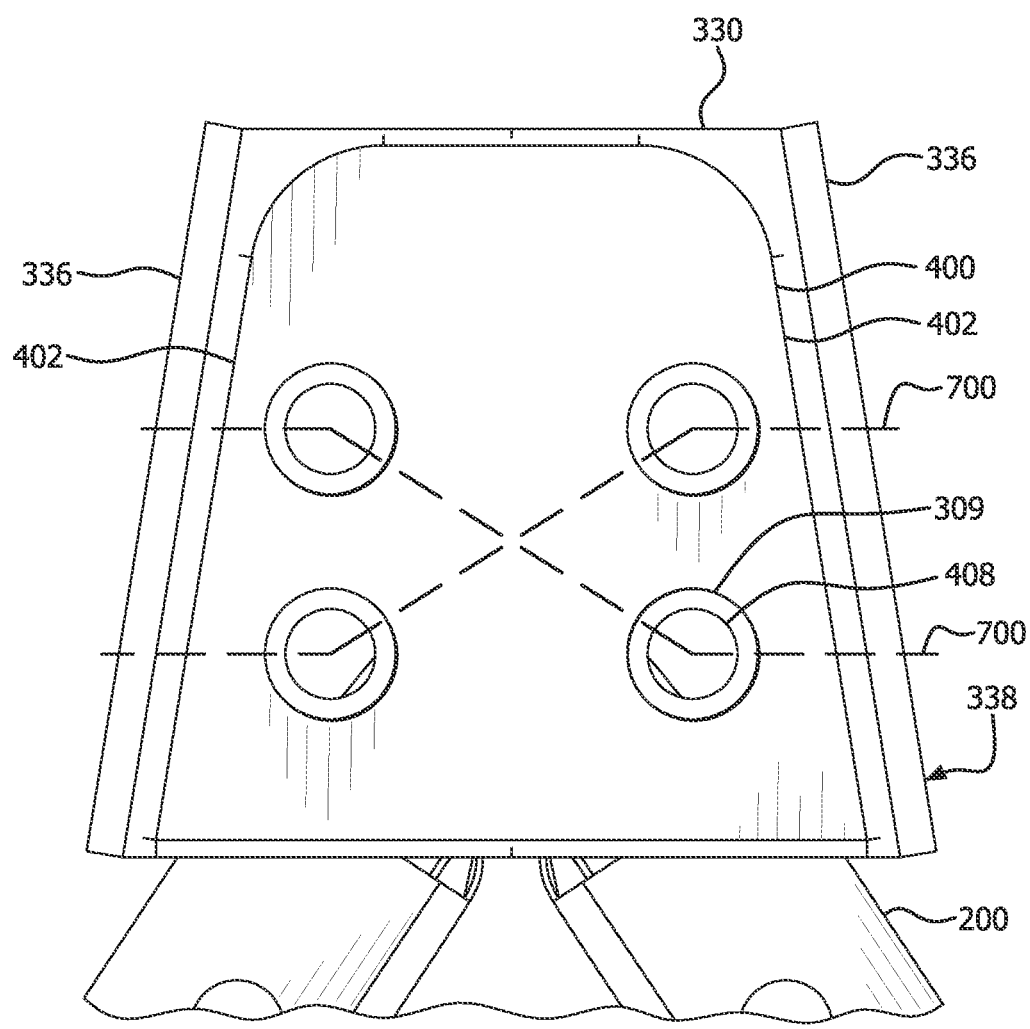
FIG. 13C is a close-up side view of the bridge region with a retention element in accordance with the embodiment of FIG. 13A.

A retention element is shown in FIGS. 8-13C. The retention element 400 is an element that is operable to be disposed within the bridge loop 338 formed by the bridge region 330 of the leaflet construct 300, which effectively prevents the bridge loop 338 from passing through the commissure slot 217, and therefore the leaflet construct 300 is mechanically coupled to the conduit 200 at the conduit outer surface 204, as shown in FIGS. 13A-13C. The retention element 400 has a width that is larger than a width of the commissure slot 217. With the retention element 400 being disposed in the bridge loop 338, the bridge loop 338 will be prevented from passing through the commissure slot 217, as shown in FIG. 11. The size of the bridge loop 338 should correspond closely to the size of the retention element 400 to prevent a portion of the bridge region 330 from extending through the commissure slot 217 to the conduit lumen 206 in case of the suture at the commissure slot 217 loosening or failing.

In accordance with an embodiment, each bridge region 330 is wrapped around a retention element outer surface 404 to the retention element inner surface 402 of one of the retention elements 400 with the bridge first end 332 wrapped across the retention element inner surface 402 to adjacent a dividing line 416 that vertically bisects the retention element 400, from a first direction and the bridge second end 334 wrapped across the retention element inner surface 402 to adjacent the dividing line 416 from an opposite direction, wherein the bridge first end 332 and bridge second end 334 are adjacent to each other to define a coaptation neck 340.

In accordance with an embodiment, the retention element 400 defines a relatively flat generally rectangular shape so as to have a low profile on the conduit outer surface 204 at the commissure slot 217. Due to the curvature of the conduit 200 at the commissure 346, the sides of the retention element 400 are formed at an angle corresponding to the two loop fold lines 336 that form an angle alpha, as shown in FIG. 12, in accordance with an embodiment.

In accordance with embodiments as shown in FIG. 7, the retention element 400 can be flat, relatively flat, or concave on a conduit facing surface to correspond with the radially outer convexity of the conduit 200 at the commissure slot 217 that the retention element 400 will be adjacent to.

The retention element 400 may be coupled to the conduit 200 at the commissure slot 217, with, such as, but not limited to, suture, adhesive, thermal bonding, or other means.

In accordance with embodiments, the conduit 200 at the commissure slot 217, the bridge region 330, and the retention elements 400 have matching and radially aligned apertures for receiving suture 700. The bridge regions 330 containing a retention element 400 are coupled to the conduit 200 by suturing through these matching apertures. The dashed lines in FIG. 13C show an illustrative suture pattern. The suturing work-load is very light and not skill-demanding, especially if the apertures are created with automated equipment is accordance with a predetermined pattern. This is compared with suturing through the conduit 200 and leaflets 310 or leaflet constructs 300 without pre-formed apertures.

Referring to FIG. 13C, each retention element 400 has a plurality of retention element apertures 408 that align with commissure slot apertures 209, as shown in FIG. 11, wherein the retention element 400 is placed against the conduit outer surface 204 at the commissure slot 217 with a portion of the bridge region 330 therebetween. A securement structure, such as, but not limited to suture 700, may be used to couple the retention element 400 to the conduit 200 at the commissure slot 217. Stitching comprising suture 700 may be passed through these aligned commissure slot apertures 209 and retention element apertures 408 and the bridge aperture 309 to hold each retention element 400 and the bridge region 330 to the conduit 200 at the commissure slot 217. Some or all of this suture 700 may pass through the leaflet attachment edge 326 of the leaflet 310. In that event, the suture 700 will contribute to securing the leaflet base 325 to the conduit 200.

Examples of suitable materials for the retention elements 400 include various biocompatible alloys such as titanium, Elgiloy, MP35N, stainless steel, nitinol, etc., and various biocompatible engineering plastics such as acetyl polymers, and PEEK.

In accordance with another embodiment, the retention element comprises a curable material that is applied in a fluid state and cured in place in and/or around the bridge loop 338 after the bridge loop 338 is assembled to the commissure slot 217.

Support Frame

Figure 15:
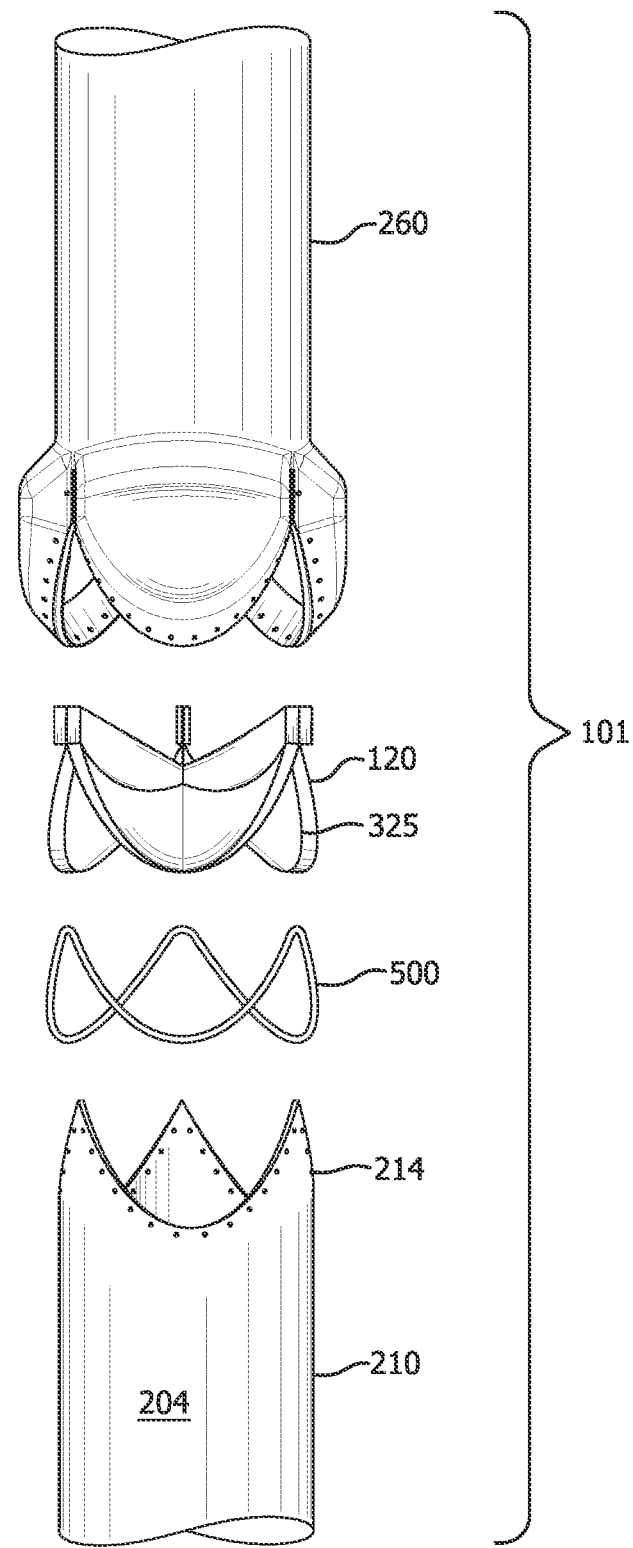
FIG. 15 is an exploded side view of an embodiment of a valved conduit including a support ring.
Figure 16:
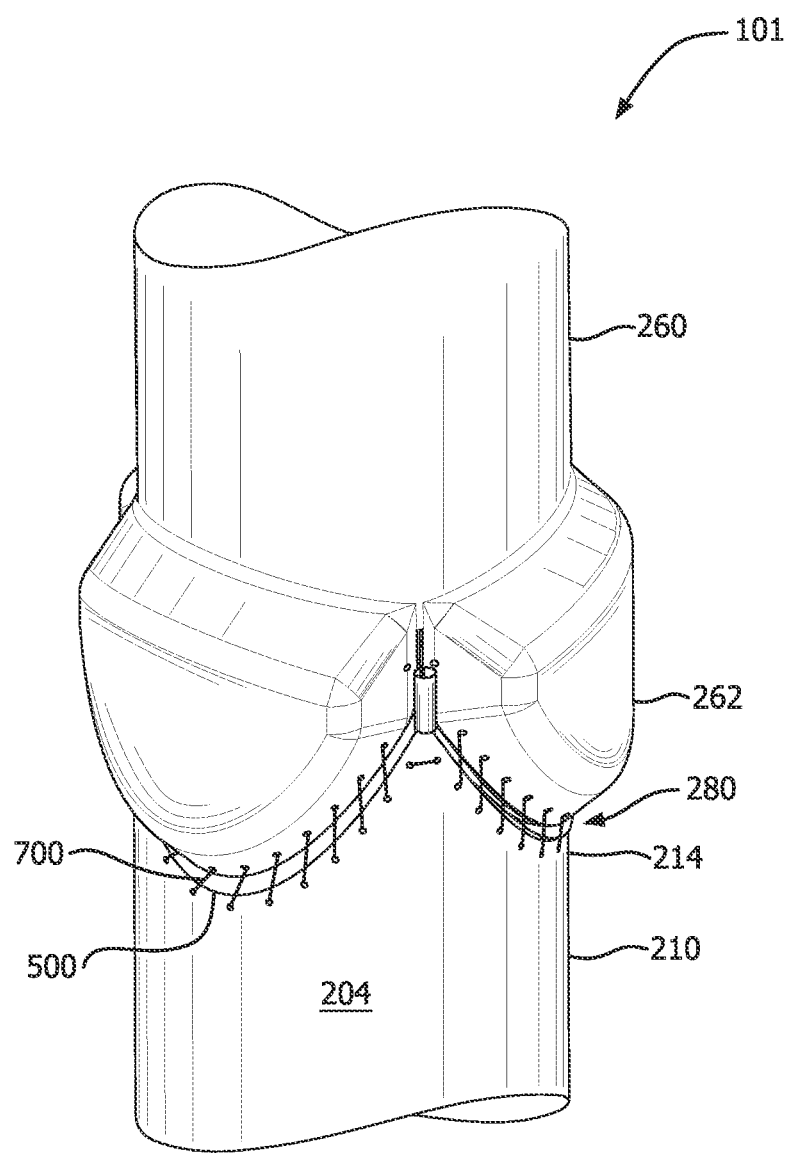
FIG. 16 is a side view of a valved conduit coupled using suture at the junction, in accordance with another embodiment.

In accordance with an embodiment, a valved conduit 101 further comprises a support frame 500 coupled to conduit outer surface 204 at the junction 280. FIG. 15 is an exploded side view, and FIG. 16 is a side view of a valved conduit 101, in accordance with an embodiment. The valved conduit 101 comprises a first conduit 210, a leaflet construct 300, a second conduit 260 and the support frame 500. The support frame 500 is a generally annular member. The support frame 500 may provide structural, load-bearing support to the junction 280, and indirectly to the leaflet base 325. The support frame 500 defines a complementary shape of the first conduit distal end 214, and therefore, also defines a complementary shape of the leaflet base 325. The support frame 500 is operable to retain a preferred shape of the junction 280, such as but limited to, to retain a circular shape of the conduit inner surface 202 at the junction 280. The support frame 500 may prevent deformation or crushing of the junction 280 due to handling and impingement on anatomy, for example. Further, the support frame 500, if made with a radiopaque material, can be used as a positioning, orientation, and flow direction aid before and after placement under x-ray visualization techniques.

The support frame 500 lies on top of or just adjacent to the junction 280 on the conduit outer surface 204.

In accordance with an embodiment, the support frame 500 is a formed wire into an annular shape. In embodiments, the support frame 500 is etched, cut, laser cut, stamped, three-dimensional printed, among other suitable processes, into an annular structure or a sheet of material, with the sheet then formed into an annular structure.

The support frame 500 can comprise, such as, but not limited to, any elastically deformable metallic or polymeric material that is generally biocompatible. The support frame 500 can comprise a shape-memory material, such as nitinol, a nickel-titanium alloy. Other materials suitable for the support frame 500 include, but not limited to, other titanium alloys, stainless steel, cobalt-nickel alloy, polypropylene, acetyl homopolymer, acetyl copolymer, other alloys or polymers, or any other material that is generally biocompatible having adequate physical and mechanical properties to function as a support frame 500 as described herein.

The support frame 500 may be coupled to the conduit outer surface adjacent the junction 280 by any suitable means. In accordance with an embodiment, the suture 700 that is used to couple the first conduit distal end 214, the valve structure 120, and the second conduit proximal end 262 is also used to capture the support frame 500 against the conduit outer surface 204 and couple it to the junction 280.

It is appreciated that other elements or means for coupling the support frame 500 to the conduit outer surface 204 are anticipated. By way of example, but not limited thereto, other means, such as mechanical and adhesive means may be used to couple the support frame 500 to the conduit outer surface 204.

Valved Conduit Embodiments

In accordance with an embodiment, a valved conduit 100 comprises the first conduit 210, the second conduit 260, and the valve structure 120, that are coupled together at the junction 280.

In accordance with an embodiment, a valved conduit 100 comprises the first conduit 210, the second conduit 260, the valve structure 120, and support frame 500, that are coupled together at the junction 280.

In accordance with an embodiment, a valved conduit 100 comprises the first conduit 210, the second conduit 260, the leaflet construct 300, that are coupled together at the junction 280, and a plurality of retention elements 400.

In accordance with an embodiment, a valved conduit 100 comprises the first conduit 210, the second conduit 260, the leaflet construct 300, and a support frame 500, that are coupled together at the junction 280, and a plurality of retention elements 400.

In accordance with an embodiment, leaflets 310 are attached to a conduit 200 that comprises a rigidified region 804 that includes rigidified bulging sinuses 575 in an efficient manner. The conduit 200 is cut proximal to the sinuses 575 in the rigidified region 804, see FIG. 17, creating a junction 280, resulting in a first conduit 210 and a second conduit 260. Wherein the conduit 200 outside of the rigidified region 804 is rather flexible, the conduit 200 at the rigidified region 804 is made to be more rigid so as to support the circular shape of the conduit lumen 206 as well as better retain the shape of the sinuses 575. The junction 280 in the olgive region 806 is defined by the shape of the cut line of the conduit 200. This allows the shape of the leaflet base 325 to be precisely defined. The leaflet 310 extends through the junction 280 of the conduit 200 to the conduit outer surface 204. Suture 700 is used to attach the leaflets 310 to the conduit 200 and the first conduit 210 and the second conduit 260 to each other. This provides a strong attachment between the leaflet 310 and the conduit 200 by allowing ePTFE suture to pass through the leaflet 310 twice, that is, on both the inside and outside of the conduit 200 as well as passing through the total thickness of the conduit 200. The rigidified region 804 of the conduit 200 provides radial compressive strength while the conduit outer surface 204 is atraumatic to adjacent tissue. The use of precision cut conduit and pre-located apertures for passing suture allows for ease of manufacturing. The valved conduit, in accordance with embodiments herein, requires minimal components and materials, for example, but not limited to, ePTFE conduit, leaflet material, ePTFE suture, and seam sealant.

Methods

A method of making a valved conduit, comprising providing a leaflet construct defining a plurality of leaflets each having a free edge and a leaflet attachment edge adjacent a leaflet base, adjacent leaflets being coupled together by a bridge region. Forming a leaflet aperture inner row and a leaflet aperture outer row of leaflet apertures adjacent the attachment edge, Providing a conduit and cutting the conduit along a parting line into a first conduit having a first conduit distal end and a second conduit having a second conduit proximal end, wherein the parting line proscribes a predetermined pattern suitable for a leaflet base. Providing a support frame having the shape substantially that of the parting line. Forming a plurality of commissure slots. Forming a plurality of apertures adjacent the first conduit distal end and the second conduit proximal end. Positioning the first conduit distal end and the second conduit proximal end adjacent thereto with the attachment edge of the leaflet therebetween. Suturing along the parting line of the conduit by advancing in one of the apertures in the first conduit, through a leaflet aperture of a leaflet aperture inner row, out through one of the apertures in the second conduit, over the outer diameter of the support frame, and then through a leaflet aperture of a leaflet aperture outer row. Repeating the suturing with the next set of apertures along the entire parting line. Tensioning the suture to adjoin the parting line of the first conduit distal end and the second conduit proximal end with the leaflet attachment edge disposed in the junction.

The method further comprises sealing the parting line and apertures in the conduit.

The method further comprises forming a commissure region in the leaflet attachment edge adjacent the free edge, and disposing the commissure region of the leaflet attachment edge into commissure slots in the second conduit proximal end.

The method further comprises forming a loop in the commissure region of the leaflet, and disposing a retention element within the loop after disposing the commissure region into the commissure slot.

Example

By way of example, an embodiment of a valved conduit was made as follows:

A leaflet material was prepared having a membrane layer of ePTFE with a porous structure that was filled with a fluoroelastomer using an imbibing process. More specifically, the membrane layer of ePTFE had been subjected to temperatures at or above the crystalline melt temperature of PTFE and was manufactured according to the general teachings described in U.S. Pat. No. 7,306,729. The ePTFE membrane was tested in accordance with the methods described elsewhere. The ePTFE membrane had a mass per area of about 0.57 g/m2, a porosity of about 90.4%, a thickness of about 2.5 µm, a bubble point of about 458 KPa, a matrix tensile strength of about 339 MPa in the longitudinal direction and about 257 MPa in the transverse direction. The porous structure of this membrane was filled with a fluoroelastomer using an imbibing process, where the fluoroelastomer was formulated according to the general teachings described in U.S. Pat. No. 7,462,675. The copolymer used consisted essentially of between about and 70 weight percent perfluorom ethyl vinyl ether and complementally about 35 and 30 weight percent tetrafluoroethylene.

The percent weight of the fluoroelastomer relative to the ePTFE was about 53%. The fluoroelastomer was dissolved in Novec HFE7500 (3M, St Paul, MN, USA) in an about 2.5% concentration. The solution was coated onto the ePTFE membrane using a mayer bar (while being supported by a polypropylene release film) and dried in a convection oven set to about 145° C. for about 30 seconds. After two coating steps, the resulting composite material of ePTFE/fluoroelastomer had a mass per area of about 3.6 g/m2.

A 21 mm diameter stainless steel mandrel was obtained. The mandrel was fitted with shrink tubing, and heated in a forced air oven set to 340 C for about 1 min, until the tubing conformed to the mandrel. Thirty five layers of the composite material possessing a width of at least 3 cm was wrapped around the shrink tubing with an elastomer rich side of the composite facing toward the mandrel. Another shrink tubing was fitted over the resulting wrapped mandrel. The assembly was placed in a forced air oven set to 340 C until the shrink tubing conformed to the underlying material. This final assembly was placed in a forced air oven set to 280 C for approximately one hour. The final assembly was removed from the oven and allowed to cool. The outer shrink tubing was removed.

An ePTFE conduit having an outer diameter of 22 mm and inner diameter of 20 mm was obtained. The conduit 100 was place over a 20 mm stainless steel mandrel, and compressed axially to approximately 55% of its original length, and heat treated with a $CO_2$ laser to form a center high ePTFE density section that extended approximately 20 mm in length.

Three sinuses were formed in the conduit in the high ePTFE density section at the same axial location but configured approximately 120° apart using the following technique. A three-piece blow mold was cut in a metal cylindrical tube whose inner diameter was the same as the outer diameter of the conduit. The mold was sectioned into 120° segments, with each segment including a milled hole whose perimeter defined the perimeter of the desired sinus. These segments were assembled and standard hose clamps tightened on each end of the mold. An oversize ePTFE balloon (outer diameter approximately 30 mm) was built using a known technique. The conduit was then inserted within the mold, centering its densified section over the holes in the mold. The balloon was inserted into the conduit, and pressurized to approximately 4 atm. The holes in the mold were then heated using a hot air gun having a set point of 850° F. for about 1 minute each. During this time, the conduit distended into the holes creating the sinuses. After forced air cooling, the balloon was deflated and the mold disassembled by loosening each pipe clamp at the ends of the mold.

Figure 17:
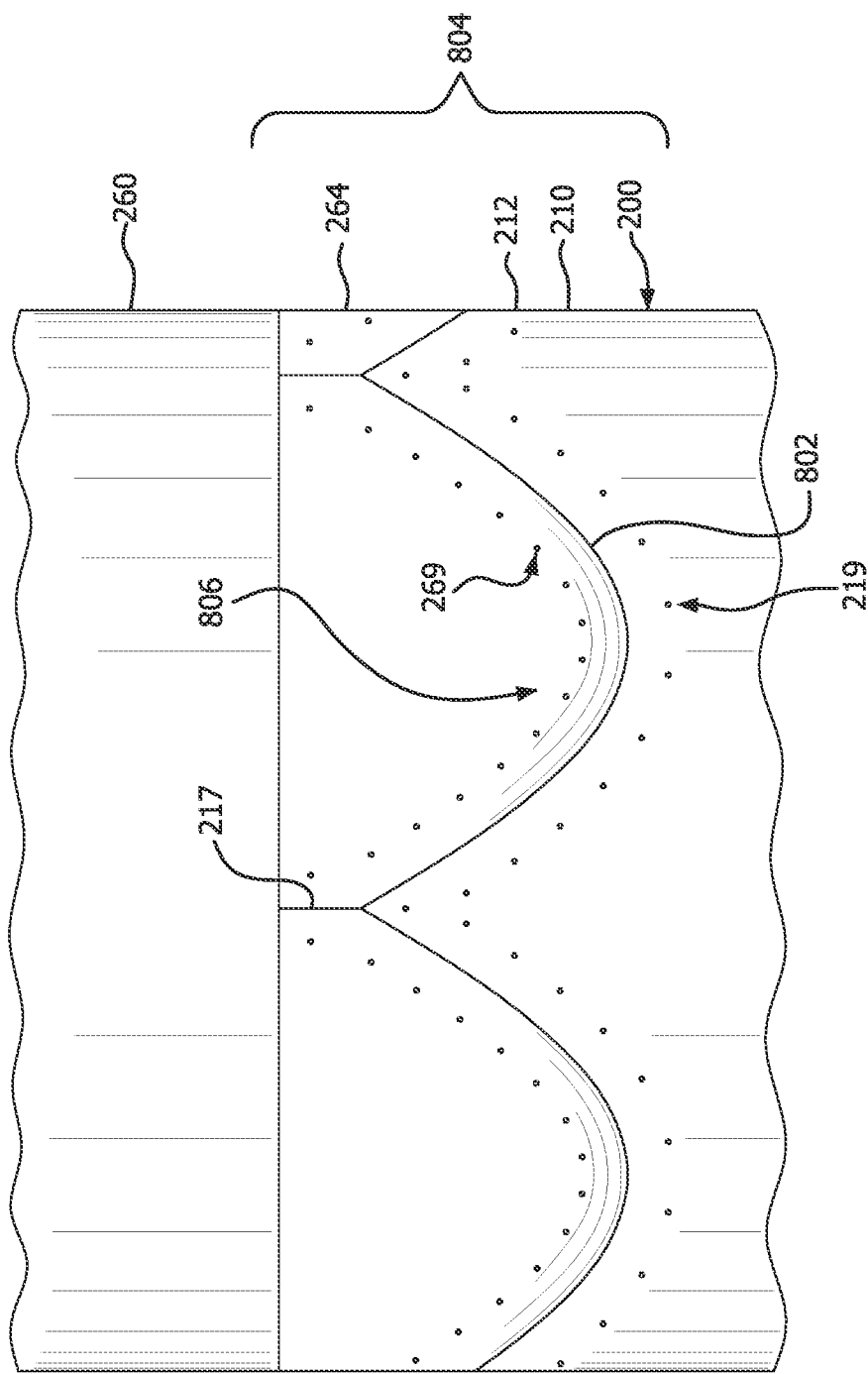
FIG. 17 is a cutting pattern for the conduit in a flat configuration in accordance with an embodiment.

On the inflow side of the sinus, the tube was cut in a pattern defining the attachment path of the leaflets, including the commissure slots 217 as shown in FIG. 17. This cutting was performed using a CO2 laser, or alternatively could be performed using a sharp blade. Additionally, first conduit apertures 219 and second conduit apertures 269 were cut on either side of this parting line 802 to define a suturing path, as shown in FIG. 18.

The first conduit 210 and the second conduit 260 were placed over the ends of two 20 mm mandrels and positioned with complementary portions, that is, the first conduit distal end 214 and the second conduit proximal end 262, adjacent to one another.

Figure 18:
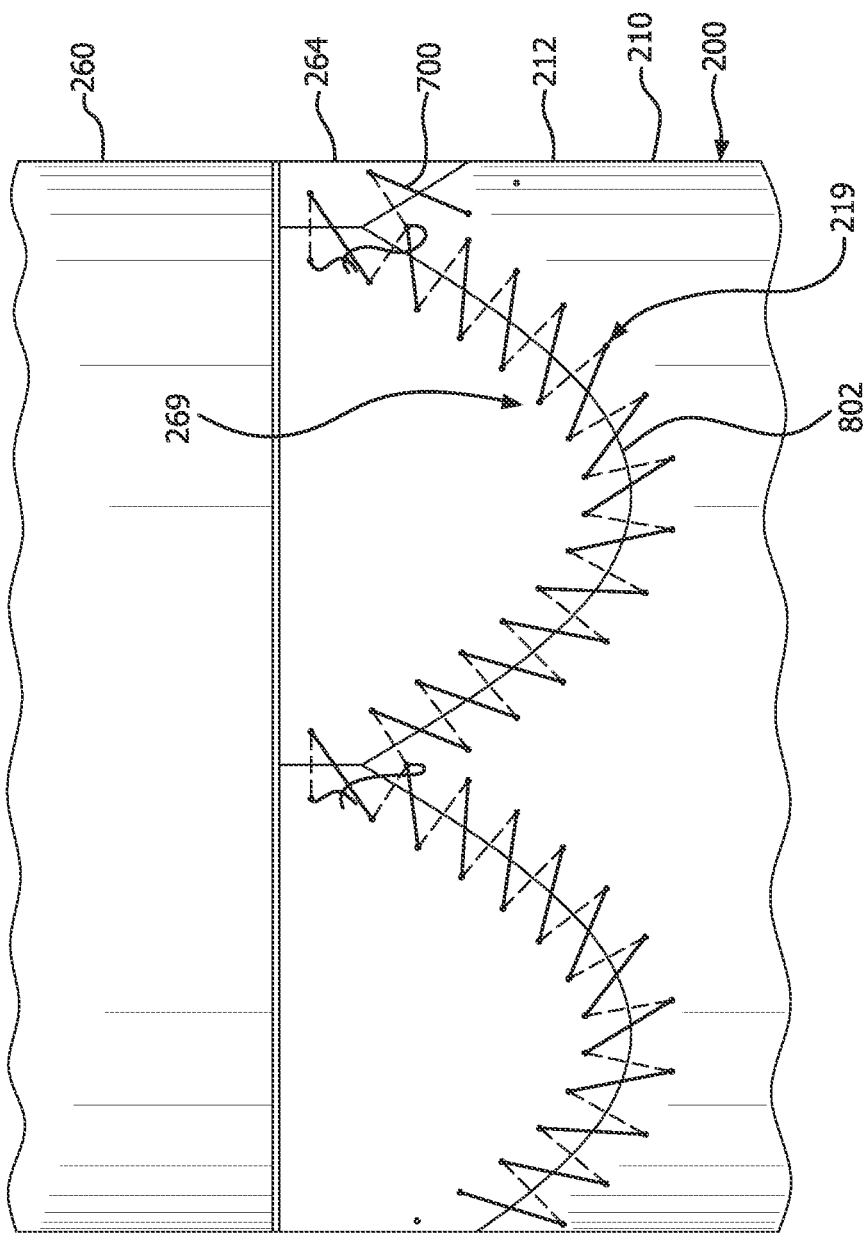
FIG. 18 is a suture pattern for the embodiment of the cutting pattern of the embodiment of FIG. 17.

The leaflet pattern as shown in FIG. 6, including the leaflet apertures 342, was cut into the leaflet material using a CO2 laser, in a pattern to correspond to the parting line and apertures for the suturing path in the conduit, as shown in FIG. 18. The leaflet apertures in the leaflet had offset apertures for the suture corresponding to both the conduit inner surface and the conduit outer surface of the conduit 200. These leaflet apertures distribute the load bearing stress to both the conduit inner surface 202 and the conduit outer surface 204 of the conduit.

A support frame was made from Nitinol wire which was wound and shape set using conventional techniques. The two ends of the wire frame were coupled using welding. The frame had a shape matching the parting line 802 of the conduit 200.

The conduit sections (first conduit and second conduit), leaflets, and support frame were assembled by using a suture (e.g., GORE-TEX Suture CV-6). Three sutures were used, one per each leaflet attachment. The first conduit distal end and the second conduit proximal end were positioned approximately 2 cm apart, and the suturing was started using a pattern progressing along the parting line 802 of the conduit 200 as shown in FIG. 18. The suturing pattern advanced by going in one of the apertures in the first conduit, through a leaflet aperture of a leaflet aperture inner row in the leaflet, out through one of the apertures in the second conduit, over the outer diameter of the support frame, and then through a leaflet aperture of a leaflet aperture outer row in the leaflet. This pattern is repeated with the next set of holes along the entire junction.

After completing suturing of the pattern, the suture was progressively tensioned around its circumference to adjoin the parting line (junction) of the first conduit distal end and the second conduit proximal end with the leaflets sandwiched in the middle of the junction. This sewing pattern resulted in functioning leaflets.

The parting line (junction) and apertures in the conduit were sealed by using a room temperature vulcanizing silicone applied thereto and allowed to dry for greater than 24 hours. The leaflets 310 were observed to be biased in the closed position.

What is claimed:

1. A method of making a valved conduit, comprising:
    obtaining a conduit;
    cutting the conduit into a first conduit and a second conduit along a cut line defining a first conduit distal end and a second conduit proximal end;
    defining a plurality of commissure slots in the second conduit proximal end; obtaining a material comprising one or more layers of expanded PTFE composite;

cutting a leaflet construct including a plurality of leaflets each being separated by a bridge region from the material, the leaflets defining an leaflet attachment edge; folding each of the bridge regions defining a bridge loop and a coaptation neck, the coaptation neck extending radially from a conduit inner surface;

disposing respective coaptation necks into each of the commissure slots; and suturing the first conduit distal end and the second conduit proximal end with the leaflet attachment edge therebetween defining a junction.

2. The method of claim 1, further comprising:
providing a support frame; and
coupling the support frame about the junction adjacent a conduit outer surface.

3. The method of claim 1, further comprising:
obtaining a plurality of retention elements; and
disposing a retention element into each of the bridge loops adjacent an outer surface of the conduit.

4. The method of claim 1, further comprising sealing the parting line and apertures in the conduit.

5. A method of making a valved conduit, comprising: providing a leaflet construct defining a plurality of leaflets each having a free edge and a leaflet attachment edge adjacent a leaflet base, adjacent leaflets being coupled together by a bridge region;
providing a conduit;
cutting the conduit along a parting line into a first conduit having a first conduit distal end and a second conduit having a second conduit proximal end, wherein the parting line proscribes a predetermined pattern suitable for a leaflet base, the conduit having a conduit inner surface and a conduit outer surface;
forming a plurality of commissure slots at second conduit proximal end;
forming a commissure region in the leaflet attachment edge adjacent the free edge, and
disposing the commissure region of the leaflet attachment edge into the commissure slots in the second conduit proximal end; and
coupling the first conduit distal end and the second conduit proximal end adjacent therewith with the leaflet attachment edge of the leaflet therebetween defining a junction.

6. The method of claim 5, further comprising:
providing a support frame having a shape substantially that of the parting line; and
coupling the support frame to an outer surface at a junction.

7. The method of claim 6, further comprising:
forming a plurality of apertures adjacent the first conduit distal end and the second conduit proximal end;
forming a leaflet aperture inner row and a leaflet aperture outer row of leaflet apertures adjacent the leaflet attachment edge;
suturing along the parting line of the conduit by advancing suture in one of the apertures in the first conduit distal end to the conduit inner surface, passing through a leaflet aperture of a leaflet aperture inner row, passing out through one of the apertures in the second conduit proximal end to the conduit outer surface, over an outer diameter of the support frame, and then through a leaflet aperture of a leaflet aperture outer row;
repeating the suturing with a next set of apertures along the parting line; and tension the suture to adjoin the parting line of the first conduit distal end and the second conduit proximal end with the leaflet attachment edge disposed in the junction.

8. The method of claim 5, further comprising:
forming a loop in the bridge region of the leaflet construct; and
disposing a retention element within the loop after disposing the bridge region into the commissure slot.

9. The method of claim 5, further comprising:
forming a plurality of apertures adjacent the first conduit distal end and the second conduit proximal end;
forming a leaflet aperture inner row and a leaflet aperture outer row of leaflet apertures adjacent the leaflet attachment edge;
suturing along the parting line of the conduit by advancing suture in one of the apertures in the first conduit distal end to the conduit inner surface, passing through a leaflet aperture of a leaflet aperture inner row, passing out through one of the apertures in the second conduit proximal end to the conduit outer surface, and then through a leaflet aperture of a leaflet aperture outer row;
repeating the suturing with a next set of apertures along the parting line; and tension the suture to adjoin the parting line of the first conduit distal end and the second conduit proximal end with the leaflet attachment edge disposed in the junction.

10. The method of claim 5, further comprising sealing the parting line and apertures in the conduit.

* * * * *